(12) United States Patent
Wen

(10) Patent No.: US 10,757,253 B1
(45) Date of Patent: *Aug. 25, 2020

(54) PATIENT RESPONSE DEVICES AND METHODS OF USING THE SAME

(71) Applicant: Xiao Jun Wen, Norcross, GA (US)

(72) Inventor: Xiao Jun Wen, Norcross, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/654,899

(22) Filed: Oct. 16, 2019

Related U.S. Application Data

(63) Continuation-in-part of application No. 16/589,060, filed on Sep. 30, 2019.

(60) Provisional application No. 62/886,816, filed on Aug. 14, 2019.

(51) Int. Cl.
| | |
|---|---|
| *G08B 23/00* | (2006.01) |
| *H04M 3/51* | (2006.01) |
| *G16H 10/60* | (2018.01) |
| *A61J 7/00* | (2006.01) |
| *A61B 5/00* | (2006.01) |

(52) U.S. Cl.
CPC ......... *H04M 3/5116* (2013.01); *A61J 7/0076* (2013.01); *A61J 7/0084* (2013.01); *G16H 10/60* (2018.01); *A61B 5/747* (2013.01); *H04M 2201/40* (2013.01); *H04M 2203/5063* (2013.01); *H04M 2242/04* (2013.01); *H04M 2242/30* (2013.01)

(58) Field of Classification Search
None
See application file for complete search history.

(56) References Cited

U.S. PATENT DOCUMENTS

| | | | | |
|---|---|---|---|---|
| 2012/0108917 | A1* | 5/2012 | Libbus | A61B 5/0006 600/301 |
| 2013/0082837 | A1* | 4/2013 | Cosentino | A61B 5/002 340/539.12 |

* cited by examiner

*Primary Examiner* — Adolf Dsouza
(74) *Attorney, Agent, or Firm* — Ming Jiang; MM IP Services LLC

(57) ABSTRACT

Present disclosure relates to a patient response device. Patient response device includes: a processor controlling operations of patient response device, a network interface controller facilitating communication among patient response device, an emergency response system server and a communication system of an emergency response system, an emergency medicine storage, and a non-volatile memory. Emergency medicine storage includes one or more emergency medicine compartments for storing one or more patient specific emergency medicines for patients. Non-volatile memory stores an operating system, a GPS module for detecting GPS location of patient carrying patient response device, and a patient response device controller. Patient response device controller includes: a patient information storage module, a patient communication control module, and computer executable instructions. Patient information storage module stores patient's information. Patient communication control module facilitates communication through the network interface controller to the emergency response system server and the communication system over a communication network.

20 Claims, 15 Drawing Sheets

PATIENT RESPONSE DEVICES AND METHODS OF USING THE SAME

CROSS-REFERENCE TO RELATED APPLICATION

This application claims priority of a provisional patent application No. 62/886,816, filed with the United States Patent and Trademark Office on Aug. 14, 2019, entitled "EMERGENCY RESCUE SYSTEM TO BE USED AT PUBLIC SPACES AND GATHERING SPACES", by Xiao-Jun Wen, and a non-provisional patent application Ser. No. 16/589,060, filed with the United States Patent and Trademark Office on Sep. 30, 2019, entitled "EMERGENCY RESPONSE SYSTEMS AND METHODS OF USING THE SAME" by Xiao Jun Wen, the disclosures of which are incorporated herein by reference in their entirety.

FIELD

The present disclosure generally relates to medical devices, and more particularly to patient response devices for emergency alert systems, emergency alert systems and methods of using the patient response devices.

BACKGROUND

According to World Health Organization (WHO), of the 56.9 million deaths worldwide in 2016, more than half (30.7 million or 54%) were due to these top three causes related to heart conditions, including ischemic heart diseases, stroke, and chronic obstructive pulmonary. Ischemic heart disease, stroke and chronic obstructive pulmonary are the world's biggest killers, accounting for a combined 18.2 million deaths in 2016. These diseases have remained the leading causes of death globally in the last 15 years.

Major of deaths from ischemic heart disease and stroke are preventable if patients call emergency medical care to get the patients to the emergency care in shortest time possible and take the appropriate medications immediately when patients start to notice some of symptoms of heart attacks and/or stroke. The most important things for a patient to survive include: the patient has access to and takes appropriate medications, the patient receives immediate professional care, and the patient is transferred to medical facilities as soon as possible before irreversible damages to the heart muscle and/or brain tissue occur.

Therefore, it is desirable to have patient response devices for high risk patient in case of an emergency to ensure: the patient's emergency is reported immediately through the patient response device, the patient receives immediate medical care by trained professionals, the patient receives instructions and takes appropriate emergency medications, and nearby emergency dispatch centers are notified and ambulance and medical emergency staff arrive at the scene in shortest possible time.

Therefore, a heretofore unaddressed needs still exist in the art to address the aforementioned deficiencies and inadequacies.

SUMMARY

In one aspect, the present disclosure relates to a patient response device. In certain embodiments, the patient response device includes: a processor, a network interface controller, an emergency medicine storage, and a non-volatile memory. The processor controls operations of the patient response device. The network interface controller facilitates the communication among the patient response device, an emergency response system server and a communication system of an emergency response system. The emergency medicine storage includes one or more emergency medicine compartments for storing one or more patient specific emergency medicines for a patient. The non-volatile memory stores an operating system, a GPS module for detecting the GPS location of the patient carrying the patient response device, and a patient response device controller. The patient response device controller includes: a patient information storage module, a patient communication control module, and computer executable instructions. The patient information storage module stores patient's information. The patient communication control module facilitates communication through the network interface controller to the emergency response system server and the communication system over a communication network.

In certain embodiments, when executed by the processor, in certain embodiments, the computer executable instructions performs one or more of following operations: receiving an emergency signal from an activated patient response device when an emergency occurs to the patient, the patient response device is activated by the patient pressing an emergency button of the patient response device, or by speaking to a microphone of the patient response device with a predetermined distinctive phrase; initiating, by the patient response device, an emergency call to a nearby emergency dispatch center to notify a live emergency responder with the patient's GPS location information and patient information including contact information of patient's helping hands on record; and connecting, by the patient response device, the patient's helping hands on record and a nearby medical facility through the patient communication control module to coordinate immediate medical assistance to the patient based on the patient information retrieved from a patient database of the emergency response system and from the patient information storage module. In certain embodiments, the computer executable instructions also performs one or more of following operations: receiving, by the patient through the patient response device, a set of patient specific medical assistance instructions from the live emergency responder for the patient to follow including instructing the patient to take one or more patient specific emergency medicines stored in the emergency medicine storage of the patient response device; and continuing, by the patient through the patient response device, communicating with the live emergency responder and the one or more patient's helping hands on record until an ambulance from the nearby medical facility arrives or the emergency is over.

In certain embodiments, the patient response device includes: at least the microphone, a speaker, and a patient response device indicator. In one embodiment, the patient uses the microphone and the speaker to make and receive voice calls. In another embodiment, the patient may use the microphone to activate the patient response device by speaking to the microphone with the predetermined distinctive phrase. When the patient is in normal condition, the patient response device indicator is in green color. When the patient is in an emergency condition, the patient activates the patient response device and the patient response device indicator is in red color.

In certain embodiments, the patient response device further includes a display screen and a camera. In one embodiment, the patient uses the display screen to receive and display text messages. In another embodiment, the patient uses the display screen and the camera to carry out videotelephony calls.

In certain embodiments, the communication among the patient, the live emergency responder, the patient's helping hands on record and the nearby medical facility includes: mobile voice calls; mobile videotelephony calls; landline voice calls; videotelephony calls over the Internet; text messages over a mobile phone; text messages over a variety of social media platforms; and videotelephony calls over the variety of social media platforms.

In certain embodiments, the communication network includes a wireless personal area network (WPAN) having a Wi-Fi network, a Bluetooth network, an infrared network, and a Zigbee network, a wireless local area network (WLAN), a wireless metropolitan area network (WMAN), a wireless wide area network (WWAN), a cellular network, and a mobile communication network.

In certain embodiments, the patient response device includes: a portable patient response device to be carried with the patient and the portable patient response device stores one or more patient specific emergency medicines, a stationary patient response device to be placed at home or work place of the patient and the stationary patient response device stores one or more patient specific emergency medicines, and a variety of public stationary patient response devices to be placed in public places, and each of the public stationary patient response devices stores at least one of a variety of common emergency medicines.

In certain embodiments, the portable patient response device includes: a lanyard holder to attach the patient response device to the patient through a lanyard, a battery charger for charging rechargeable battery, a SIM card slot having a wireless communication SIM card to support wireless communication, and an emergency flash light.

In certain embodiments, the portable patient response device may include: one or more speed dial keys to be programed for the patient to contact one or more frequent callers.

In another aspect, the present disclosure relates to an emergency response system. In certain embodiments, the emergency response system includes: an emergency response system server, a patient database, a communication system, and a set of patient response devices, one for each of a group of patients. Each of the patients and a corresponding patient response device each patient carries are registered at the emergency response system server. When an emergency occurs to a patient, the emergency response system server provides immediate emergency assistance to the patient. The patient database is connected to and accessible by the emergency response system server. The patient database stores patient information of the patients. The patient information includes: patient's personal information, patient's medical history, patient's contact information, and contact information of patient's helping hands and local medical facilities to be notified of each patient. The communication system is also connected to the emergency response system server. The communication system provides voice, text, and videotelephony over a communication network among the patient, one or more live emergency responders from a nearby emergency dispatch center, one or more patient's helping hands on record, and one or more nearby medical facilities to provide immediate emergency assistance to the patient when emergency occurs. The patient's helping hands include, but not limited to, all family members, relatives, friends, neighbors, guardians, bystanders, local emergency or non-emergency medical facilities, community rescue members and trained CPR volunteers, and anyone who is nearby and is able to offer assistance.

In certain embodiments, each patient carries the corresponding patient response device, and each patient response device includes an emergency button and a microphone for the patient to activate the patient response device and initiate at least voice communication with the emergency response system server and the communication system directly. Each patient response device also includes an emergency medicine storage for storing one or more patient specific emergency medicines to be used when emergency occurs.

In certain embodiments, each patient response device includes a patient response device indicator. This patient response device indicator is lit in green indicating the patient is in normal condition. When an emergency occurs to the patient, the patient activates the patient response device, the patient response device indicator turns red indicating the patient is in an emergency. The patient response device is activated by the patient pressing the emergency button of the patient response device, or by speaking to the microphone of the patient response device with a predetermined distinctive phrase.

In certain embodiments, when the patient response device is activated, the patient response device initiates an emergency call to the nearby emergency dispatch center to notify a live emergency responder with the patient's GPS location information and patient information including contact information of patient's helping hands on record. The live emergency responder connects to one or more patient's helping hands on record and a nearby medical facility to coordinate immediate medical assistance to the patient based on the patient information received and retrieved from the patient database. The live emergency responder and the emergency response system server provide patient specific medical assistance instructions for the patient to follow including instructing the patient to take one or more patient specific emergency medicines stored in the emergency medicine storage of the patient response device. Whenever possible, the patient continues to communicate with the live emergency responder and the one or more patient's helping hands on record until an ambulance from the nearby medical facility arrives or the emergency is over.

In certain embodiments, the emergency response system server includes: a processor for controlling operations of the emergency response system, a network interface controller connected to the communication network through a firewall connector over a firewall, and a non-volatile memory for storing an operating system, a network communication module, and an emergency response controller. The emergency response controller includes a patient information storage module for accessing the patient database through a database connector, a communication control module for facilitating communication to the communication system through a communication system connector, and computer executable instructions.

In certain embodiments, when executed by the processor, the computer executable instructions performs one or more of following operations: receiving, from the patient response device, an emergency voice call through the communication system when the patient response device is activated by the patient pressing the emergency button and the patient speaking to the microphone with a predetermined distinctive phrase when an emergency occurs, notifying the live emergency responder of the nearby emergency dispatch center of the emergency along with patient's GPS location information, and patient information including contact information of patient's helping hands on record, and connecting, via the patient response device carried by the patient, to the patient's helping hands on record and the nearby medical facility through the communication control module to coordinate immediate medical assistance to the patient.

In certain embodiments, the computer executable instructions also performs one or more of following operations: retrieving, by the patient information storage module, patient information from the patient database, transmitting, by the communication control module, a set of patient specific medical assistance instructions through the communication system connector and the live emergency responder for the patient to follow including instructing the patient to take one or more patient specific emergency medicines stored in the emergency medicine storage of the patient response device, and the patient continues to communicate with the live emergency responder and the one or more patient's helping hands on record until an ambulance from the nearby medical facility arrives or the emergency is over.

In certain embodiments, the communication system includes: a voice input module having a mobile voice input interface to receive mobile voice calls, and a landline voice input interface to receive landline voice calls, a text input module having a social media text input interface to receive text messages through the variety of social media platforms, and a text message input interface to receive text messages through mobile phones, a video input module having a mobile video input interface to receive videotelephony calls over the mobile phones, and a social media video input interface to receive videotelephony calls through the variety of social media platforms, a voice output module having a mobile voice output interface to make mobile voice calls, and a landline voice output interface to make landline voice calls, a text output module having a social media text output interface to transmit text messages through the variety of social media platforms, and a text message output interface to transmit text messages through the mobile phones, a video output module having a mobile video output interface to make videotelephony calls over the mobile phones, and a social media video output interface to make videotelephony calls through the social media platforms, a speech to text conversion module for converting voice input to text input, a live emergency responder interface module for the live emergency responder to receive and make conference calls among the patient, the live emergency responder, the patient's helping hands on record and the nearby medical facility through voice calls, text messages, and videotelephony calls, and a text to speech conversion module to make voice calls to the patient through the patient response device.

The communication system connector includes: a voice input terminal connected to the voice input module, a text input terminal connected to the text input module, a video input terminal connected to the video input module, a voice output terminal connected to the voice output module, a text output terminal connected to the text output module, and a video output terminal connected to the video output module.

In yet another aspect, the present disclosure relates to a method of using a patient response device. In certain embodiments, the method includes: registering, by a group of patients, a group of patient response devices, one corresponding patient response device for each patient, at an emergency response system server of an emergency response system. Patient information of each of the group of patients is stored in a patient database of the emergency response system, and the emergency response system includes a network of emergency dispatch centers 108 to provide immediate emergency assistance to the group of patients when emergencies occur to them.

In certain embodiments, the method also includes: activating, by a patient, the patient response device carried by the patient when an emergency occurs. The patient response device includes a patient response device indicator. When the patient is in normal condition, the patient response device indicator of the patient response device is lit in green. When an emergency occurs to the patient, the patient activates the patient response device and the patient response device turns red indicating the patient is in an emergency. The patient response device is activated by the patient pressing an emergency button of the patient response device or speaking to a microphone of the patient response device with a predetermined distinctive phrase.

In certain embodiments, once the patient response device is activated, the method includes: initiating, by the patient response device, an emergency call to a nearby emergency dispatch center to notify a live emergency responder with the patient's GPS location information and patient information including contact information of patient's helping hands on record, and connecting, by the live emergency responder, to one or more patient's helping hands on record and a nearby medical facility to coordinate immediate medical assistance to the patient based on the patient information received and retrieved from the patient database.

In certain embodiments, the method further includes: providing, by the live emergency responder and the emergency response system server, patient specific medical assistance instructions for the patient to follow including instructing the patient to take one or more patient specific emergency medicines stored in an emergency medicine storage of the patient response device; and communicating, by the patient through a communication system of the emergency response system, with the live emergency responder and the one or more patient's helping hands on record until an ambulance from the nearby medical facility arrives.

In certain embodiments, the emergency response system includes: the emergency response system server, the patient database, the communication system, and the group of patient response devices, one for each of a group of patients. Each of the patients and a corresponding patient response device each patient carries are registered at the emergency response system server. When an emergency occurs to the patient, the emergency response system server provides immediate emergency assistance to the patient. The patient database is connected to and accessible by the emergency response system server. The patient database stores patient information of the patients. The patient information includes: patient's personal information, patient's medical history, patient's contact information, and contact information of patient's helping hands and local medical facilities to be notified of each patient. The communication system is also connected to the emergency response system server. The communication system provides voice, text, and videotelephony over a communication network among the patient, one or more live emergency responders from the nearby emergency dispatch center, one or more patient's helping hands on record, and one or more nearby medical facilities to provide immediate emergency assistance to the patient when emergency occurs. The patient's helping hands include, but not limited to, all family members, relatives, friends, neighbors, guardians, bystanders, local emergency or non-emergency medical facilities, community rescue members and trained CPR volunteers, and anyone who is nearby and is able to offer assistance.

In certain embodiments, each patient carries the corresponding patient response device, and each patient response device includes the emergency button and the microphone for the patient to activate the patient response device and initiate at least voice communication with the emergency response system server and the communication system directly. The emergency medicine storage stores one or more patient specific emergency medicines to be used when emergency occurs.

In certain embodiments, the communication network includes a wireless personal area network (WPAN) having a Wi-Fi network, a Bluetooth network, an infrared network, and a Zigbee network, a wireless local area network (WLAN), a wireless metropolitan area network (WMAN), a wireless wide area network (WWAN), a cellular network, and a mobile communication network.

In certain embodiments, the emergency response system server includes: a processor for controlling operations of the emergency response system, a network interface controller connected to the communication network through a firewall connector over a firewall, and a non-volatile memory for storing an operating system, a network communication module, and an emergency response controller. The emergency response controller includes a patient information storage module for accessing the patient database through a database connector, a communication control module for facilitating communication to the communication system through a communication system connector, and computer executable instructions.

In certain embodiments, when executed by the processor, the computer executable instructions performs one or more of following operations: receiving, from the patient response device, an emergency voice call through the communication system when the patient response device is activated by the patient pressing the emergency button and the patient speaking to the microphone with a predetermined distinctive phrase when an emergency occurs, notifying the live emergency responder of the nearby emergency dispatch center of the emergency along with patient's GPS location information, and patient information including contact information of patient's helping hands on record, and connecting, via the patient response device carried by the patient, to the patient's helping hands on record and the nearby medical facility through the communication control module to coordinate immediate medical assistance to the patient.

In certain embodiments, the computer executable instructions also performs one or more of following operations: retrieving, by the patient information storage module, patient information from the patient database, transmitting, by the communication control module, a set of patient specific medical assistance instructions through the communication system connector and the live emergency responder for the patient to follow including instructing the patient to take one or more patient specific emergency medicines stored in the emergency medicine storage of the patient response device, and the patient continues to communicate with the live emergency responder and the one or more patient's helping hands on record until an ambulance from the nearby medical facility arrives or the emergency is over.

In certain embodiments, the patient response device includes at least the microphone and a speaker for the patient to make and receive voice calls and to activate the patient response device by speaking to the microphone with the predetermined distinctive phrase. The patient response device may include a display screen and a camera. In one embodiment, the patient uses the display screen to receive and display text messages. In another embodiment, the patient uses the display screen and the camera to carry out videotelephony calls.

In certain embodiments, the communication among the patient, the live emergency responder, the patient's helping hands on record and the nearby medical facility includes: mobile voice calls; mobile videotelephony calls; landline voice calls; videotelephony calls over the Internet; text messages over a mobile phone; text messages over a variety of social media platforms; and videotelephony calls over the variety of social media platforms.

In certain embodiments, the communication system connector includes: a voice input terminal connected to a voice input module, a text input terminal connected to a text input module, a video input terminal connected to a video input module, a voice output terminal connected to a voice output module, a text output terminal connected to a text output module, and a video output terminal connected to a video output module.

In certain embodiments, the patient response device includes: a portable patient response device to be carried with the patient and the portable patient response device stores one or more patient specific emergency medicines, a stationary patient response device to be placed at home or work place of the patient and the stationary patient response device stores one or more patient specific emergency medicines, and a variety of public stationary patient response devices to be placed in public places, and each of the public stationary patient response devices stores at least one of a variety of common emergency medicines.

These and other aspects of the present disclosure will become apparent from the following description of the preferred embodiment taken in conjunction with the following drawings, although variations and modifications therein may be effected without departing from the spirit and scope of the novel concepts of the disclosure.

BRIEF DESCRIPTION OF THE DRAWINGS

The accompanying drawings illustrate one or more embodiments of the present disclosure, and features and benefits thereof, and together with the written description, serve to explain the principles of the present invention. Wherever possible, the same reference numbers are used throughout the drawings to refer to the same or like elements of an embodiment, and wherein.

DETAILED DESCRIPTION

Figure 1:
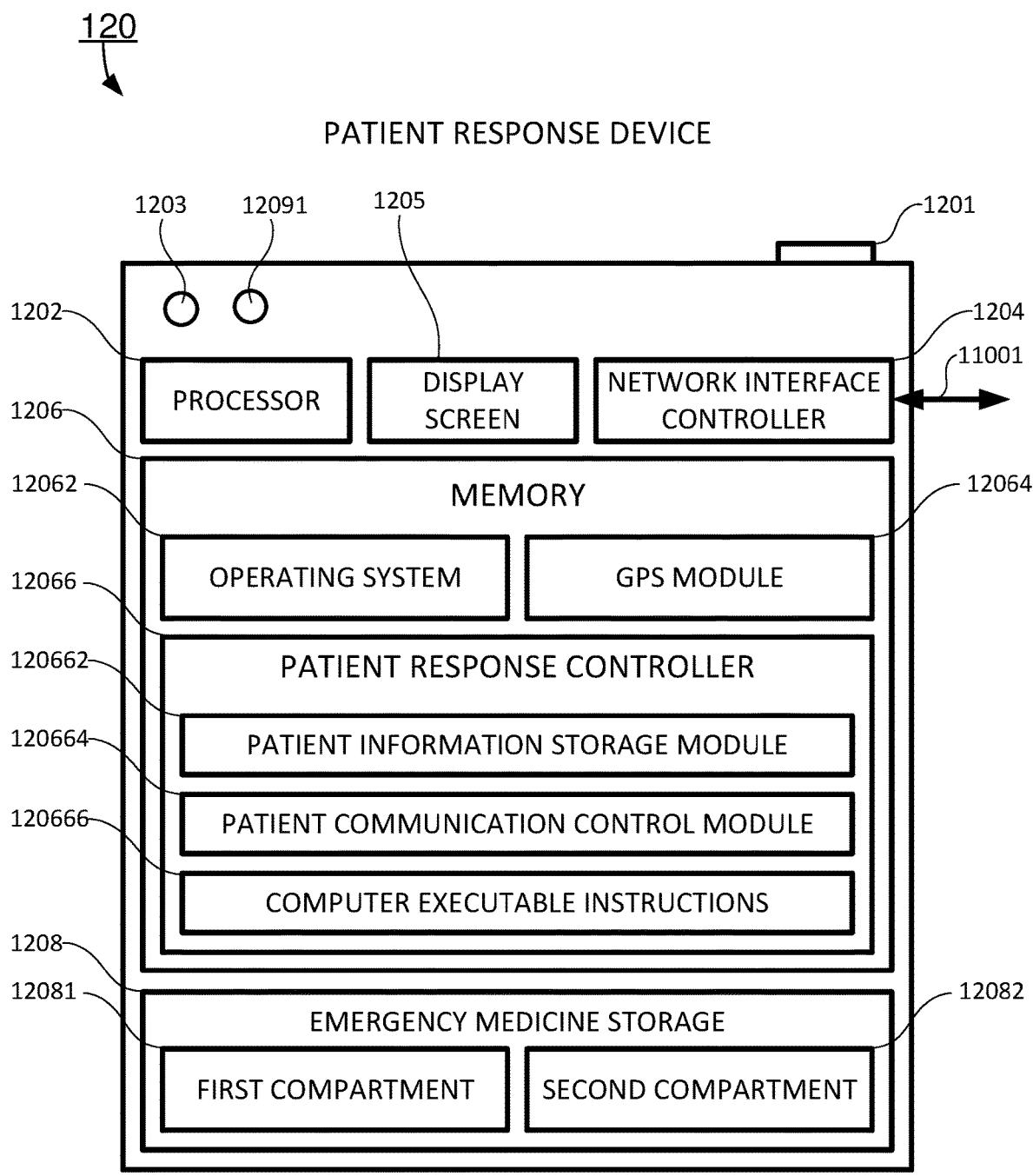
FIG. 1 shows a block diagram of a patient response device according to certain embodiments of the present disclosure.

The present disclosure is more particularly described in the following examples that are intended as illustrative only since numerous modifications and variations therein will be apparent to those skilled in the art. Various embodiments of the disclosure are now described in detail. Referring to the drawings, like numbers, if any, indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present disclosure. Additionally, some terms used in this specification are more specifically defined below.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the disclosure or of any exemplified term. Likewise, the disclosure is not limited to various embodiments given in this specification.

Unless otherwise defined, all technical and scientific terms used herein have the same meaning as commonly understood by one of ordinary skill in the art to which this disclosure pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, "plurality" means two or more.

As used herein, the term "helping hands" is defined as, but not limited to: all family members, relatives, friends, neighbors, guardians, bystanders, local emergency or non-emergency medical facilities, community rescue members and trained CPR volunteers, and anyone who is nearby and able to help.

As used herein, the terms "comprising," "including," "carrying," "having," "containing," "involving," and the like are to be understood to be open-ended, i.e., to mean including but not limited to.

As used herein, the phrase at least one of A, B, and C should be construed to mean a logical (A or B or C), using a non-exclusive logical OR. It should be understood that one or more steps within a method may be executed in different order (or concurrently) without altering the principles of the present disclosure.

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code; other suitable hardware components that provide the described functionality; or a combination of some or all of the above, such as in a system-on-chip. The term module may include memory (shared, dedicated, or group) that stores code executed by the processor.

The term code, as used above, may include software, firmware, and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

The present disclosure will now be described more fully hereinafter with reference to the accompanying drawings FIGS. 1 through 15, in which embodiments of the disclosure are shown. This disclosure may, however, be embodied in many different forms and should not be construed as limited to the embodiments set forth herein; rather, these embodiments are provided so that this disclosure will be thorough and complete, and will fully convey the scope of the disclosure to those skilled in the art. Like numbers refer to like elements throughout.

In one aspect, the present disclosure relates to a patient response device 120. In certain embodiments, as shown in FIG. 1, the patient response device 120 includes: a processor 1202, a network interface controller 1204, an emergency medicine storage 1208, and a non-volatile memory 1206. The processor 1202 controls operations of the patient response device 120. The network interface controller 1204 facilitates the communication among the patient response device 120, an emergency response system server 102 and a communication system 104 of an emergency response system 100.

In certain embodiments, the emergency medicine storage 1208 includes one or more emergency medicine compartments. In one embodiment, as shown in FIG. 1, the emergency medicine storage 1208 includes a first compartment 12081 and a second compartment 12082. These emergency medicine compartments are used to store the patient specific emergency medicines. Various sizes of emergency medicine storage 1208 of patient response devices 120 may be available to accommodate various size emergency medicines for various high-risk patients 130 with various known diseases.

In certain embodiments, the non-volatile memory 1206 stores an operating system 12062, a GPS module 12064 for detecting the GPS location of the patient 130 carrying the patient response device 120, and a patient response device controller 12066 having a patient information storage module 120662 for storing the patient's information, a patient communication control module 120664 for facilitating communication through the network interface controller 1204 to the emergency response system server 102 and the communication system 104 over the communication network 110, and computer executable instructions 120666.

In certain embodiments, when executed by the processor 1202, the computer executable instructions 120666 performs one or more of following operations, not necessarily in the following order:

the patient response device 120 is activated by the patient 130 by pressing the emergency button 1201 of the patient response device 120, or speaking to the microphone 12091 of the patient response device 120 with the predetermined distinctive phrase, when an emergency occurs; When the emergency button 1201 is pressed for a predetermined period of time by the patient 130, the patient response device 120 initiate at least voice communication with the emergency response system server 102 and the communication system 104 directly. In one embodiment, the predetermined period of time may be set as three seconds. When the patient 130 presses the emergency button 1201 for longer than three seconds, the patient response device 120 determines that the patient 130 does have an emergency. When the patient 130 presses the emergency button 1201 for less than three seconds, the patient response device 120 determines that the patient 130 does not have an emergency, and the emergency button 1201 was pressed by accident. This is designed to distinguish a real emergency and a false alarm.

In certain embodiments, each patient response device 120 includes the microphone 12091 for the patient 130 to activate the emergency response device 120 through a voice-activated emergency call function when an emergency occurs. To activate the emergency response device 120 through the voice-activated emergency call function, the patient 130 is required to speak to the microphone 12091 with a predetermined distinctive phrase to avoid false alarm by mis-activating the emergency response device 120 by noise around the patient 130. In one embodiment, the patient 130 may speak to the microphone: "hello, doctor", for example. Other phrase may be selected for different countries, or different languages. When the patient response device 120 receives the predetermined distinctive phrase, the patient response device 120 initiate at least voice communication with the emergency response system server 102 and the communication system 104 directly.

the patient response device 120 initiates an emergency call to a nearby emergency dispatch center 108 to notify a live emergency responder 1081 with the patient's GPS location information and patient information including contact information of one or more patient's helping hands on record;

the patient response device 120 is connected to the patient's helping hands on record and a nearby medical facility through the patient communication control module 120664 to coordinate immediate medical assistance to the patient 130 based on the patient information retrieved from the patient database 106 and from the patient information storage module 120662;

the patient response device 120 receives a set of patient specific medical assistance instructions from the live emergency responder 1081 for the patient 130 to follow including instructing the patient to take one or more patient specific emergency medicines stored in the emergency medicine storage 1208 of the patient response device 120; and the patient 130 continues to communicate with the live emergency responder 1081 and the one or more patient's helping hands on record until an ambulance from the nearby medical facility arrives or the emergency is over.

In certain embodiments, the patient response device 120 includes: at least the microphone 12091, a speaker 12092, and a patient response device indicator 1203. In one embodiment, the patient 130 uses the microphone 12091 and the speaker 12092 to make and receive voice calls. In another embodiment, the patient 130 may use the microphone 12091 to activate the patient response device 120 by speaking to the microphone 12091 with the predetermined distinctive phrase when an emergency occurs. When the patient 130 is in normal condition, the patient response device indicator 1203 is in green color. When the patient 130 is in an emergency condition, the patient activates the patient response device 120 and the patient response device indicator 1203 is in red color.

In certain embodiments, the patient response device 120 further includes a display screen 1205 and a camera 12093. In one embodiment, the patient 130 uses the display screen 1205 to receive and display text messages. In another embodiment, the patient 130 uses the display screen 1205 and the camera 12093 to carry out videotelephony calls. In certain embodiments, the communication among the patient 130, the live emergency responder 1081, the patient's helping hands on record and the nearby medical facility includes: mobile voice calls; mobile videotelephony calls; landline voice calls; videotelephony calls over the Internet; text messages over a mobile phone; text messages over a variety of social media platforms; and videotelephony calls over the variety of social media platforms.

In certain embodiments, the social media platforms include, but not limited to: Facebook, Youtube, WhatsApp, Messenger, WeChat, Instagram, QQ, Tumblr, Qzone, Tik Tok, Sina Weibo, Twitter, Reddit, Baidu Tieba, LinkedIn, Viber, Snappchat, and Pinterest and various combination of these social media platforms.

In certain embodiments, the communication network 110 includes a wireless personal area network (WPAN) having a Wi-Fi network, a Bluetooth network, an infrared network, and a Zigbee network, a wireless local area network (WLAN), a wireless metropolitan area network (WMAN), a wireless wide area network (WWAN), a cellular network, and a mobile communication network.

In one embodiment, the patient response device 120 includes a portable patient response device to be carried with the patient 130. The portable patient response device stores one or more patient specific emergency medicines for the patient 130. In another embodiment, the patient response device 120 includes a stationary patient response device to be placed at home or work place of the patient 130. The stationary patient response device 120 stores one or more patient specific emergency medicines for the patient 130. In yet another embodiment, the patient response device 120 includes multiple public stationary patient response devices 120. These public stationary patient response devices 120 are placed in public places. Each of the public stationary patient response devices 120 stores at least one of several common emergency medicines.

Figure 2:
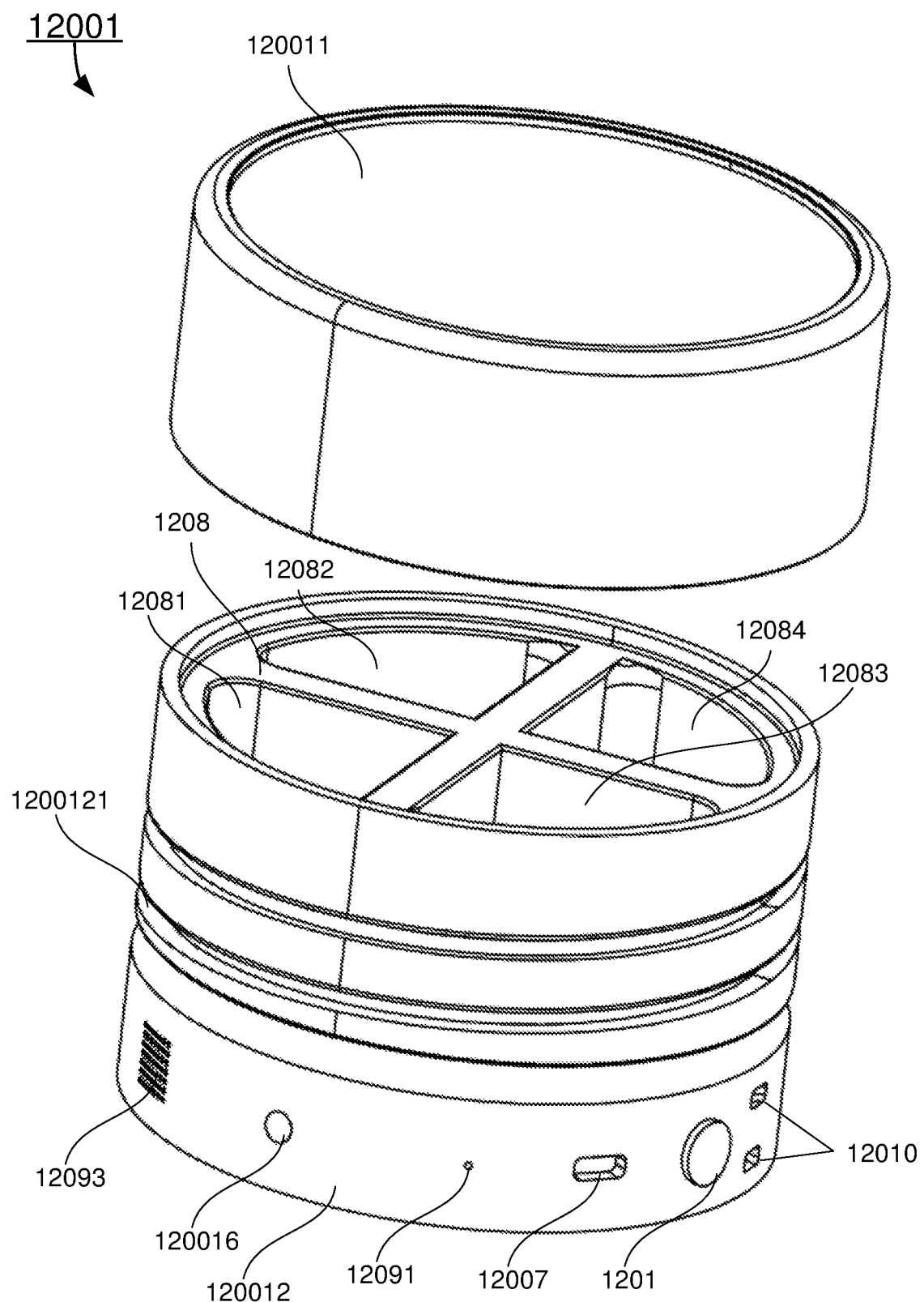
FIG. 2 illustrates a perspective exploded view of an exemplary patient response device according to one embodiment of the present disclosure.
Figure 3:
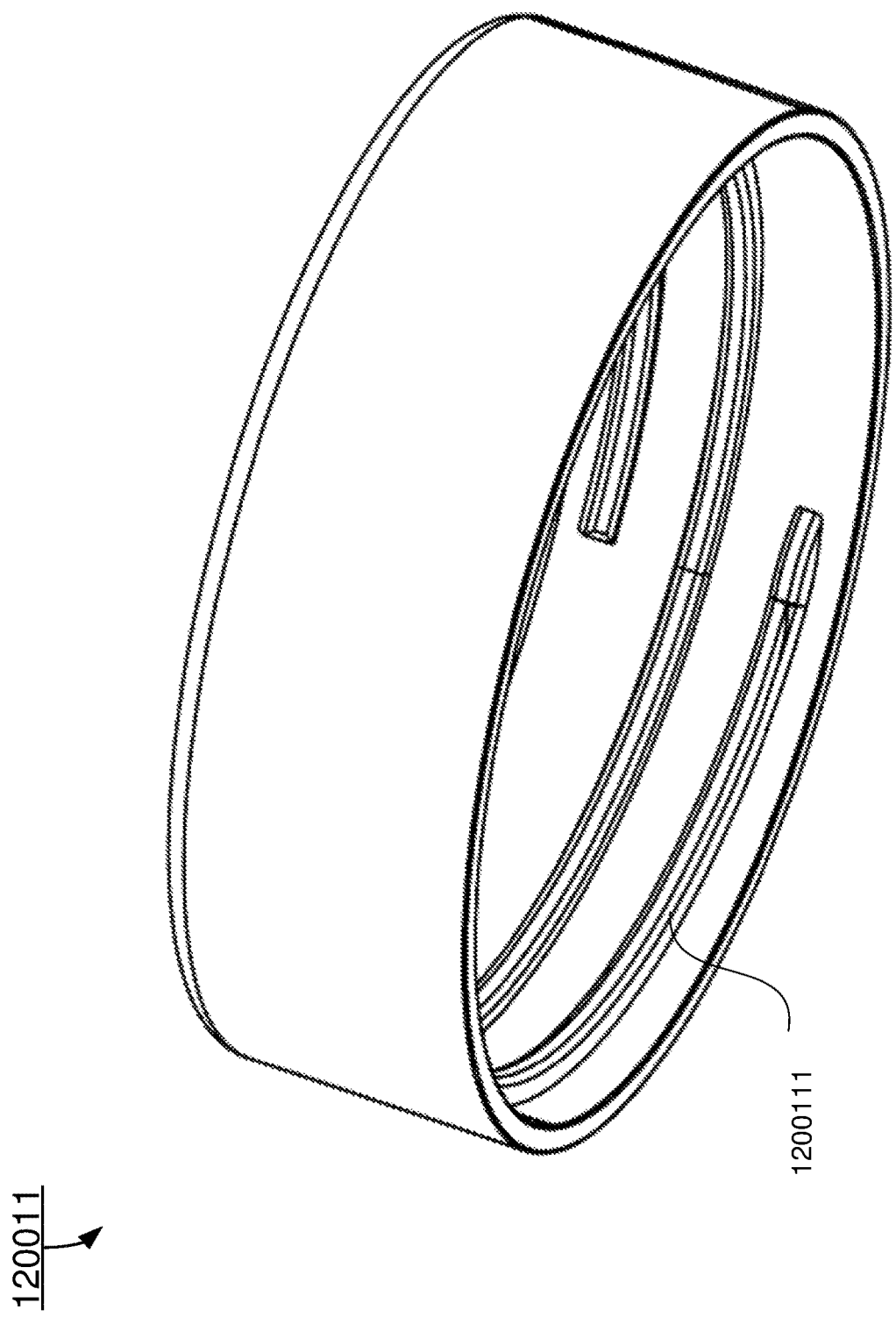
FIG. 3 illustrates a bottom perspective view of a patient response device cap having an internal thread to close the patient response device according to the embodiment of the present disclosure as shown in FIG. 2.

Referring to FIGS. 2 through 5, an exemplary patient response device 12001 is shown according to a first embodiment of the present disclosure. This patient response device 12001 is in a round shape, and the patient response device 12001 includes a cap 120011 and a base 120012 as shown in FIG. 2. The base 120012 includes an external thread 1200121. As shown in FIG. 3, the cap 120011 includes an internal thread 1200111. The cap 120011 can close the patient response device 120 through engagement of the internal thread 1200111 of the cap 120011 and the external thread 1200121 of the base 120012.

Figure 4:
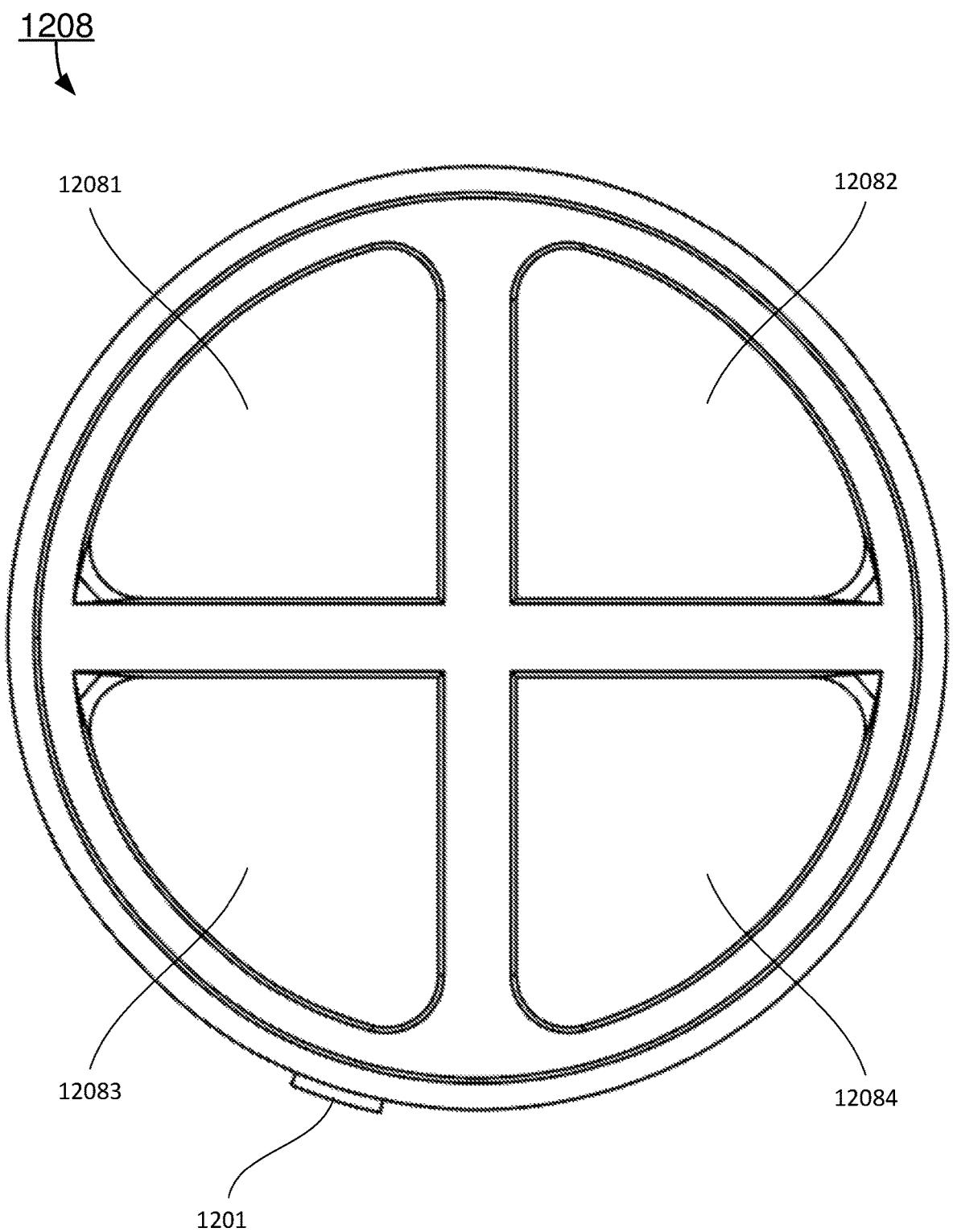
FIG. 4 illustrates a top plan view of an emergency medicine storage having 4 emergency medicine compartments according to the embodiment of the present disclosure as shown in FIG. 2.

In certain embodiments, the top of the base 120012 includes an emergency medicine storage 1208. The emergency medicine storage 1208, as shown in FIG. 4, includes four different emergency medicine compartments: a first emergency medicine compartment 12081, a second emergency medicine compartment 12082, a third emergency medicine compartment 12083, and a fourth emergency medicine compartment 12084. These emergency medicine compartments are used to store several patient specific emergency medicines. The emergency medicine storage 1208 may also configured in different sizes and shapes according to the needs of specific patient 130.

Figure 5:
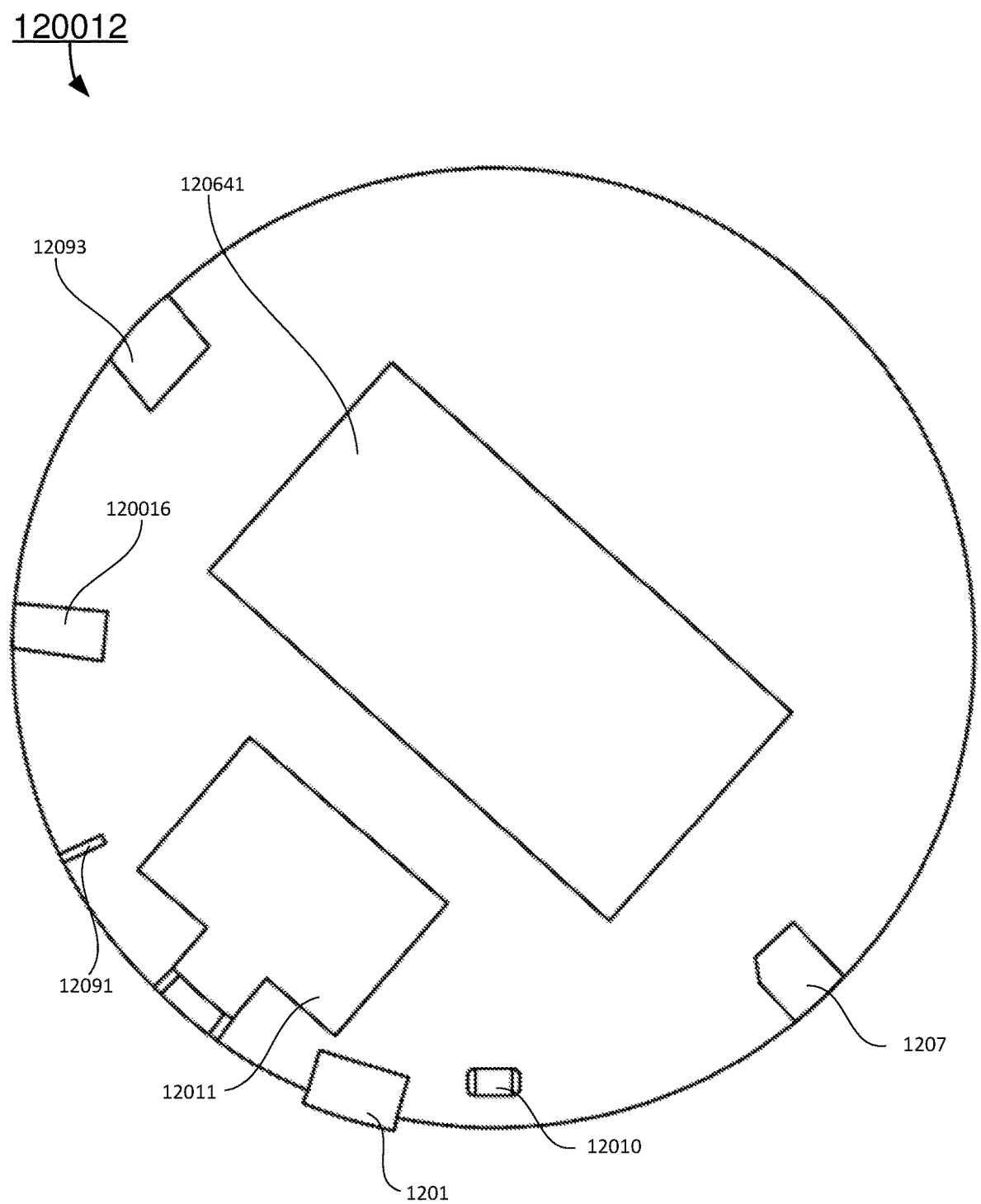
FIG. 5 illustrates a top plan view of a patient response device base according to the embodiment of the present disclosure as shown in FIG. 2.

In certain embodiments, as shown in FIG. 5, the bottom portion of the base 120012 includes an electronic circuit board 120641 having a GPS module 12064 installed to control the operation of the patient response device 12001, and a SIM Card slot 1207 having a SIM card installed to facilitate wireless communications. In certain embodiments, the bottom portion of the base 120012 includes: an emergency button 1201 for the patient 130 to press when an emergency occurs, a microphone 12091 for the patient 130 to speak to for voice calls and for activating the patient response device 12001, a speaker 12092 for the patient 130 to make and receive voice calls.

In certain embodiments, also as shown in FIG. 5, the bottom portion of the base 120012 includes: a battery compartment 12011 to place a battery or a rechargeable battery, and an emergency flash light 120016 to be used in a dark environment. In certain embodiments, the bottom portion of the base 120012 also includes one or two lanyard holes 12010 for the patient 130 to use a lanyard to attach the patient response device 12001 to the body of the patient 130.

Figure 6:
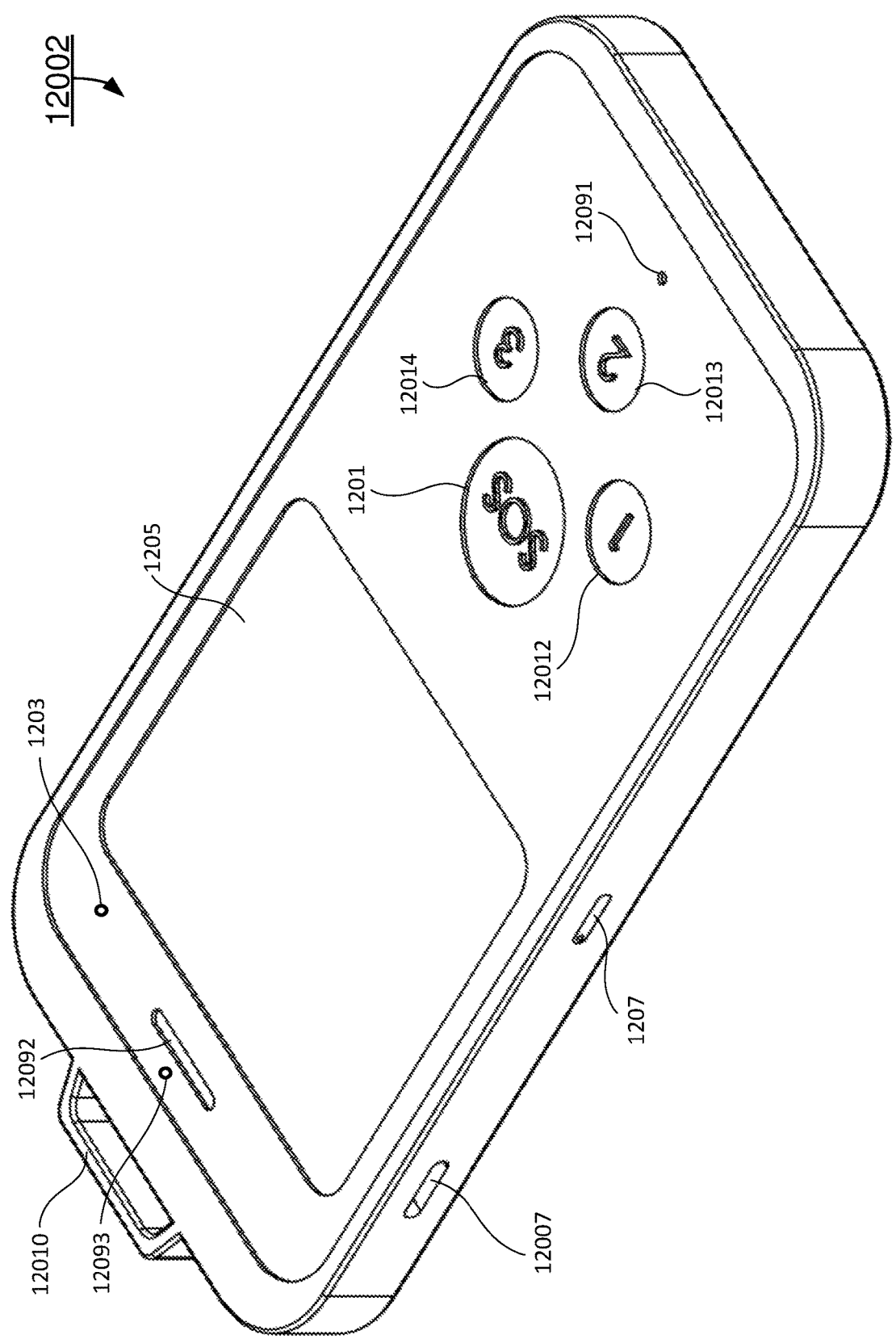
FIG. 6 illustrates a top left perspective view of another exemplary patient response device according to another embodiment of the present disclosure.
Figure 7:
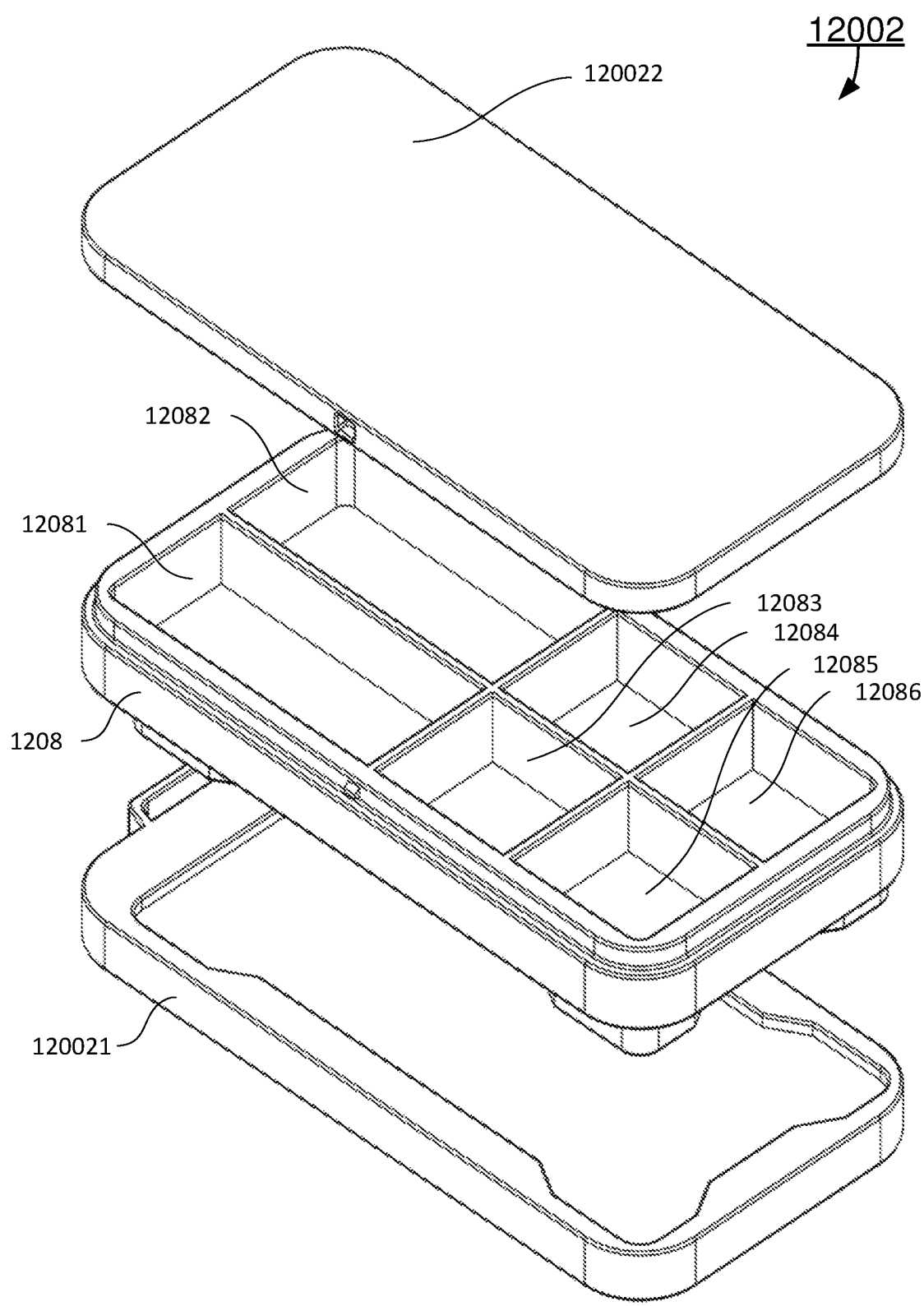
FIG. 7 illustrates a bottom exploded perspective view of the patient response device according to the embodiment of the present disclosure as shown in FIG. 6.
Figure 8:
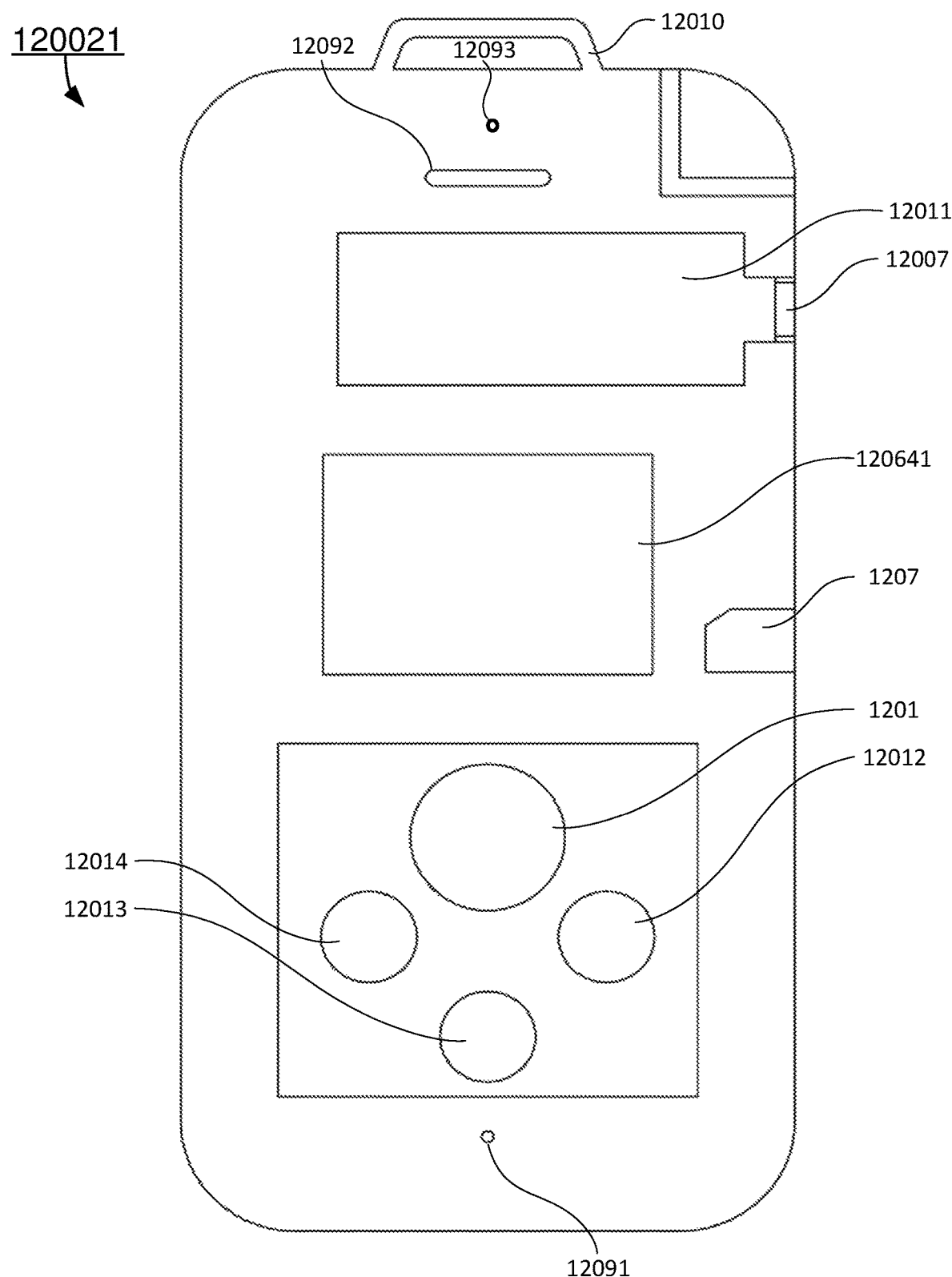
FIG. 8 illustrates an inside bottom plan view of a top cover of the patient response device according to the embodiment of the present disclosure as shown in FIG. 6.

Referring to FIGS. 6 through 8, another exemplary patient response device 12002 is shown according to a second embodiment of the present disclosure. This patient response device 12002 is in a rectangular shape, like a cell phone. The patient response device 12002 includes a top cover 120021, an emergency medicine storage 1208, and a bottom cover 120022, as shown in FIG. 7.

In certain embodiments, the emergency medicine storage 1208, as shown in FIG. 7, includes six different emergency medicine compartments: a first emergency medicine compartment 12081, a second emergency medicine compartment 12082, a third emergency medicine compartment 12083, a fourth emergency medicine compartment 12084, a fifth emergency medicine compartment 12085, and a sixth emergency medicine compartment 12086. These emergency medicine compartments are used to store several patient specific emergency medicines. The emergency medicine storage 1208 may also configured in other sizes and shapes according to the needs of specific patient 130.

In certain embodiments, as shown in FIG. 8, the top cover 120021 of the patient response device 12002 includes an electronic circuit board 120641 having a GPS module 12064 installed to control the operation of the patient response device 12002, and a SIM Card slot 1207 having a SIM card installed to facilitate wireless communications. In certain embodiments, the top cover 120021 of the patient response device 12002 includes: an emergency button 1201 for the patient 130 to press when an emergency occurs, a microphone 12091 for the patient 130 to speak to for voice calls and for activating the patient response device 12002, a speaker 12092 for the patient 130 to make and receive voice calls.

In certain embodiments, the patient response device 12002 may include: one or more speed dial keys 12012, 12013, and 12014 to be programed for the patient 130 to contact one or more frequent callers.

In certain embodiments, also as shown in FIG. 8, the top cover 120021 of the patient response device 12002 includes: a battery compartment 12011 to place a battery or a rechargeable battery, an external power supply/battery charger 12007, a lanyard holder 12010 for the patient 130 to use a lanyard to attach the patient response device 12002 to the body of the patient 130.

In certain embodiments, the patient response device 12002 may include a display screen 1205 and a camera 12093 as shown in FIG. 6. In one embodiment, the patient 130 uses the display screen 1205 to receive and display text messages. In another embodiment, the patient 130 uses the display screen 1205 and the camera 12093 to carry out videotelephony calls.

Figure 9:
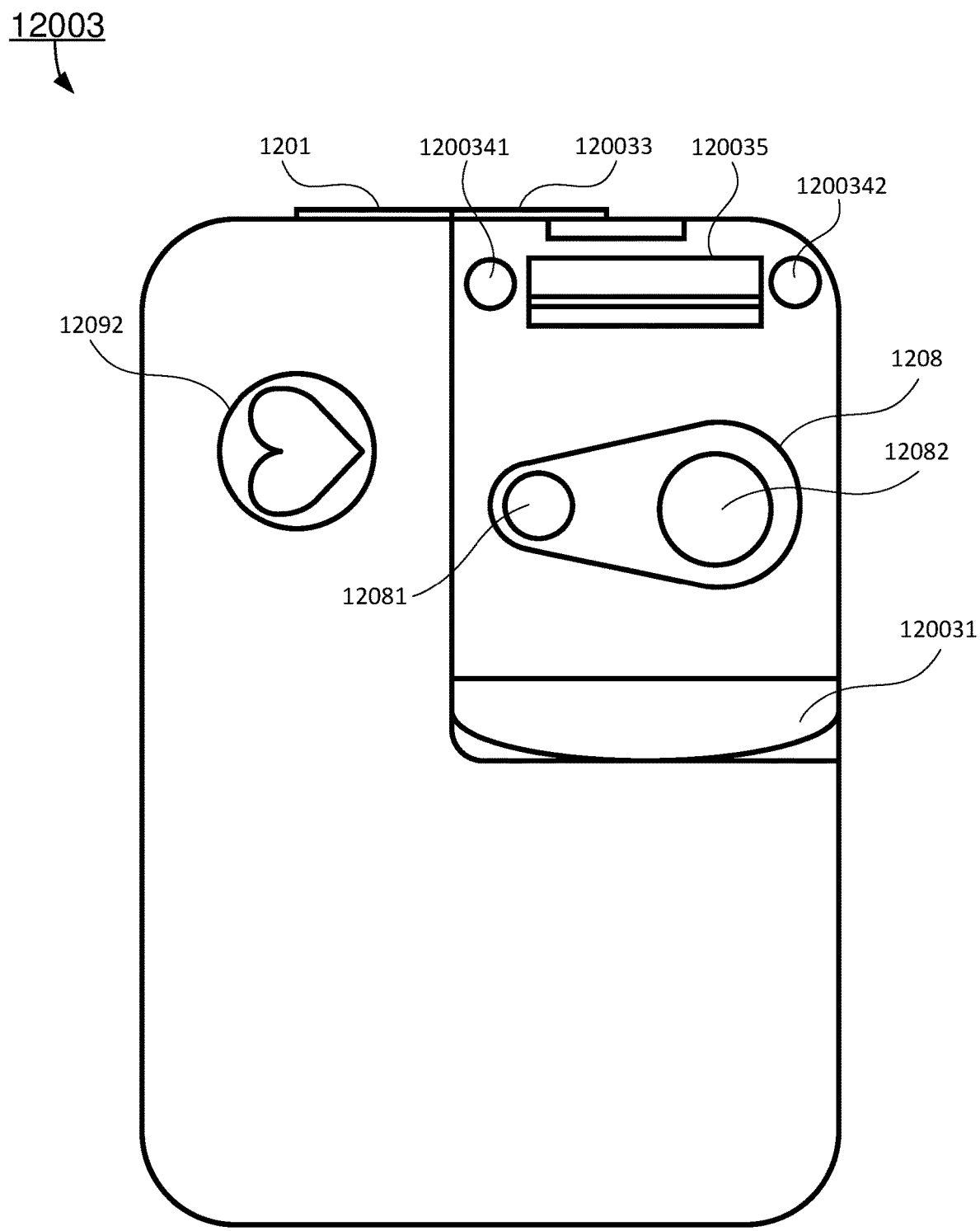
FIG. 9 illustrates a front elevation view of yet another exemplary patient response device with an emergency medicine storage lid open according to yet another embodiment of the present disclosure.
Figure 10:
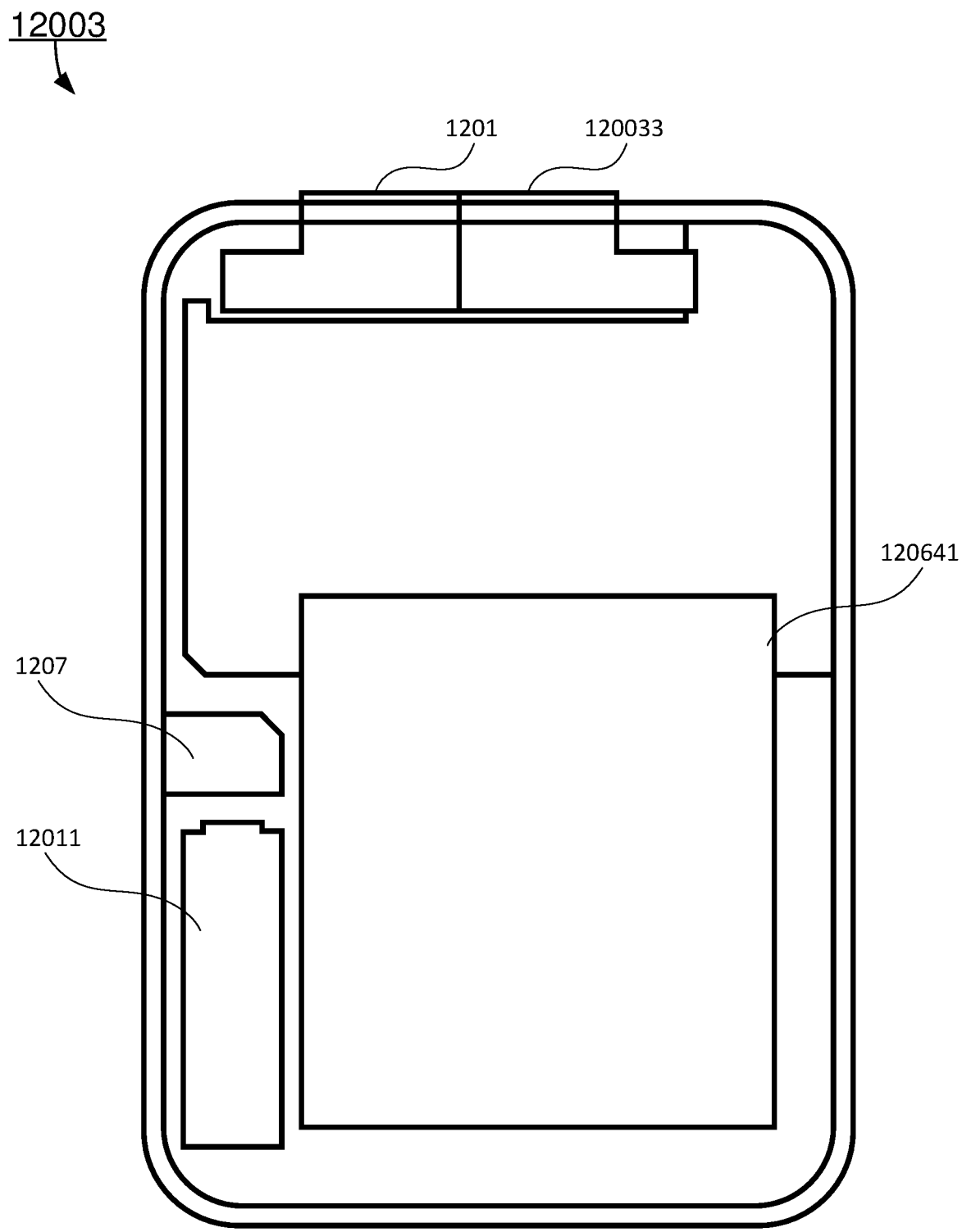
FIG. 10 illustrates a bottom inside plan view of the patient response device according to the embodiment of the present disclosure as shown in FIG. 9.
Figure 11:
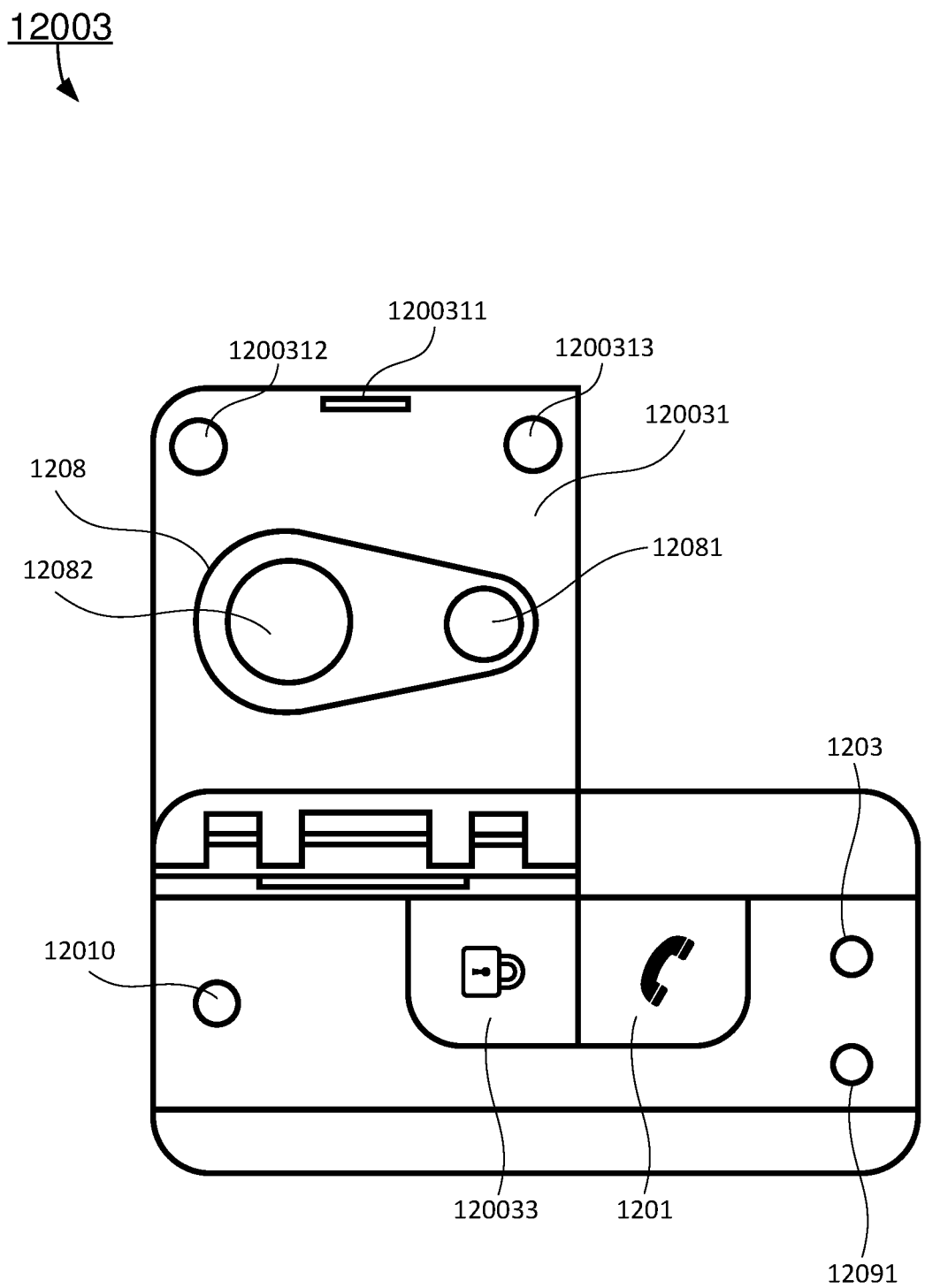
FIG. 11 illustrates a top plan view of the patient response device having the top cover of the patient response device open according to the embodiment of the present disclosure as shown in FIG. 9.

Referring to FIGS. 9 through 11, a front elevation view of yet another exemplary patient response device 12003 with an emergency medicine storage lid 120031 open according to a third embodiment of the present disclosure. This patient response device 12002 is in a rectangular shape, like a car key fob. The patient response device 12003 includes an emergency medicine storage lid 120031 that covers an emergency medicine storage 1208, as shown in FIGS. 9 and 11. When the emergency medicine storage lid 120031 is open, the emergency medicine storage 1208 is exposed and the emergency medicine storage 1208, includes two different emergency medicine compartments: a first emergency medicine compartment 12081, and a second emergency medicine compartment 12082. These emergency medicine compartments are used to store several patient specific emergency medicines. The emergency medicine storage 1208 may also configured in other sizes and shapes according to the needs of specific patient 130. When the emergency medicine storage lid 120031 is open, as shown in FIG. 9, the emergency medicine storage 1208 includes a first positioning pin 1200341 and a second positioning pin 1200342. When the emergency medicine storage lid 120031 is open, as shown in FIG. 11, the emergency medicine storage lid 120031 includes: an emergency medicine storage lid lock pin 1200311, a first positioning hole 1200312, and a second positioning hole 1200313. The emergency medicine storage 1208 has an emergency medicine storage lid lock 120035. When the emergency medicine storage lid 120031 is closed, the emergency medicine storage lid lock pin 1200311 is inserted into the emergency medicine storage lid lock 120035 to lock the emergency medicine storage lid 120031. The first positioning hole 1200312 and the second positioning hole 1200313 are engaged with the first positioning pin 1200341 and the second positioning pin 1200342, respectively to lock the emergency medicine storage lid 120031. The patient response device12003 includes an emergency medicine storage lock release button 120033. When the patient 130 is instructed to take the emergency medicines, the patient 130 presses the emergency medicine storage lock release button 120033, the first positioning hole 1200312 and the second positioning hole 1200313 are disengaged with the first positioning pin 1200341 and the second positioning pin 1200342, respectively to unlock and open the emergency medicine storage lid 120031 to access the emergency medicines stored in the emergency medicine storage 1208.

In certain embodiments, a top portion of the patient response device 12003 includes: an emergency button 1201 for the patient 130 to press when an emergency occurs. Front portion of the patient response device 12003 includes a speaker 12092 for the patient 130 to carry out voice calls.

In certain embodiments, as shown in FIG. 10, the patient response device 12003 includes: an electronic circuit board 120641 having a GPS module 12064 installed to control the operation of the patient response device 12003, a SIM Card slot 1207 having a SIM card installed to facilitate wireless communications, and a battery compartment 12011 to place a battery or a rechargeable battery.

In certain embodiments, as shown in FIG. 11, the patient response device 12003 includes: a microphone 12091 for the patient 130 to speak to for voice calls and for activating the patient response device 12001, and a patient response device indicator 1203. The patient response device indicator 1203 is lit in green indicating the patient 130 is in normal condition. When an emergency occurs to the patient 130, the patient 130 activates the patient response device 120, the patient response device indicator 1203 turns red indicating the patient 130 is in an emergency. The patient response device 120 is activated by the patient 130 pressing the emergency button 1201 of the patient response device 120, or by speaking to the microphone 12091 of the patient response device 120 with a predetermined distinctive phrase. The patient response device 12003 may also include: a lanyard holder 12010 for the patient 130 to use a lanyard to attach the patient response device 12002 to the body of the patient 130.

Figure 12:
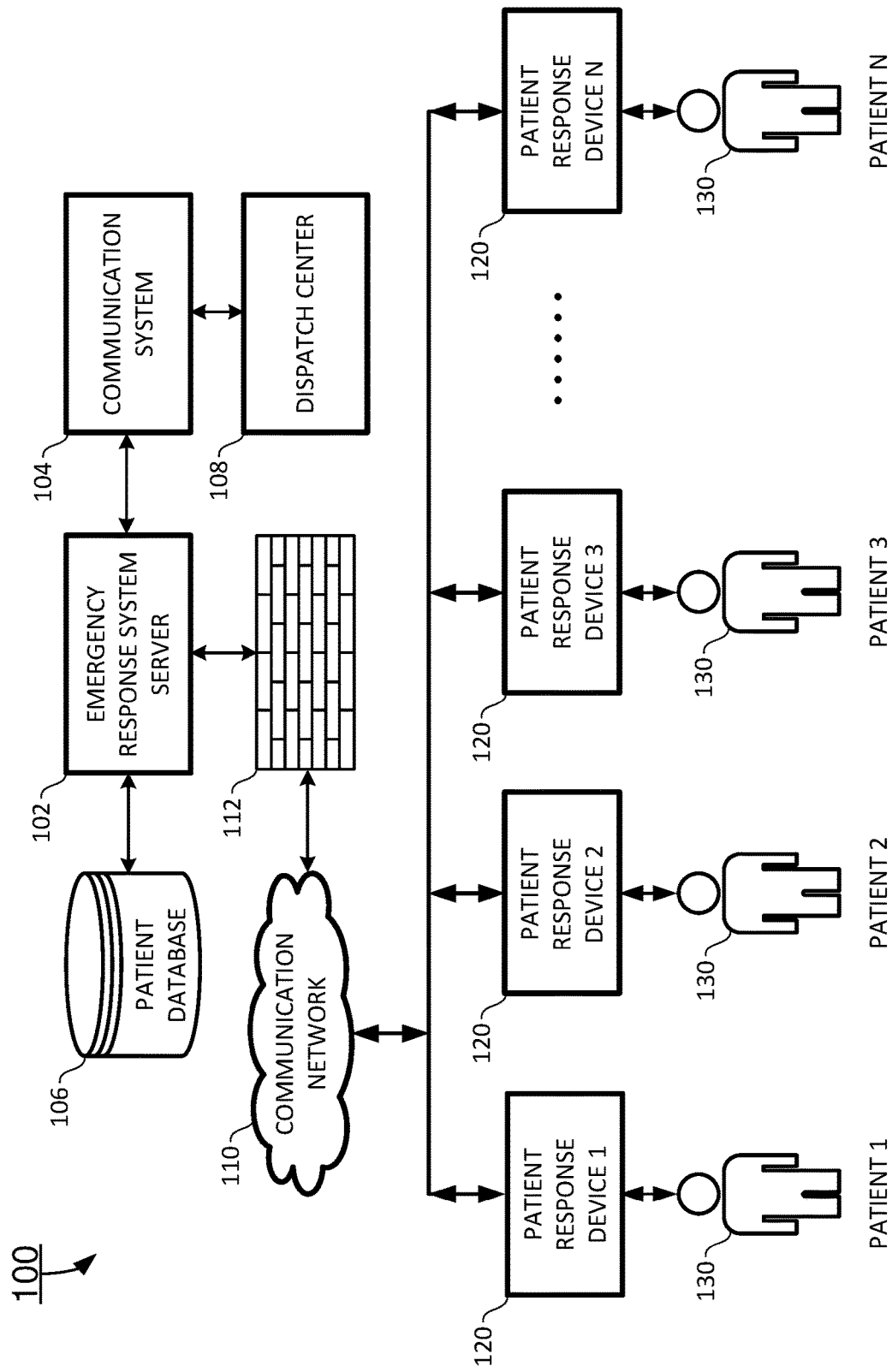
FIG. 12 illustrates a block diagram of an emergency response system according to certain embodiments of the present disclosure.

In another aspect, the present disclosure relates to an emergency response system 100 as shown in FIG. 12. In certain embodiments, the emergency response system 100 includes: an emergency response system server 102, a patient database 106, a communication system 104, and a set of patient response devices 120, one for each of a group of patients 130. Each of the patients 130 and a corresponding patient response device 120 each patient 130 carries are registered at the emergency response system server 102. When an emergency occurs to a patient 130, the emergency response system server 102 provides immediate emergency assistance to the patient 130. The patient database 106 is connected to and accessible by the emergency response system server 102. The patient database 106 stores patient information of the patients 130. The patient information includes: patient's personal information, patient's medical history, patient's contact information, and contact information of patient's helping hands and local medical facilities to be notified of each patient 130.

In certain embodiments, the communication system 104 is also connected to the emergency response system server 102. The communication system 104 provides voice, text, and videotelephony over a communication network 110 among the patient 130, one or more live emergency responders 1081 from a nearby emergency dispatch center 108, one or more patient's helping hands on record, and one or more nearby medical facilities to provide immediate emergency assistance to the patient 130 when emergency occurs. The patient's helping hands include, but not limited to, all family members, relatives, friends, neighbors, guardians, bystanders, local emergency or non-emergency medical facilities, community rescue members and trained CPR volunteers, and anyone who is nearby and is able to offer assistance.

In certain embodiments, each patient 130 carries a corresponding patient response device 120, and each patient response device 120 includes an emergency button 1201 and a microphone 12091 for the patient 130 to activate the patient response device 120 and initiate at least voice communication with the emergency response system server 102 and the communication system 104 directly. Each patient response device also includes an emergency medicine storage 1208 for storing one or more patient specific emergency medicines to be used when emergency occurs.

In certain embodiments, each patient response device 120 includes a patient response device indicator 1203, as shown in FIG. 1. This patient response device indicator 1203 is lit in green indicating the patient 130 is in normal condition. When an emergency occurs to the patient 130, the patient 130 activates the patient response device 120, the patient response device indicator 1203 turns red indicating the patient 130 is in an emergency. The patient response device 120 is activated by the patient 130 pressing the emergency button 1201 of the patient response device 120, or by speaking to the microphone 12091 of the patient response device 120 with a predetermined distinctive phrase.

In certain embodiments, when the patient response device 120 is activated, the patient response device 120 initiates an emergency call to the nearby emergency dispatch center 108 to notify a live emergency responder 1081 with the patient's GPS location information and patient information including contact information of patient's helping hands on record. The live emergency responder 1081 connects to one or more patient's helping hands on record and a nearby medical facility to coordinate immediate medical assistance to the patient 130 based on the patient information received and retrieved from the patient database 106. The live emergency responder 1081 and the emergency response system server 102 provide patient specific medical assistance instructions for the patient 130 to follow including instructing the patient 130 to take one or more patient specific emergency medicines stored in the emergency medicine storage 1208 of the patient response device 120. Whenever possible, the patient 130 continues to communicate with the live emergency responder 1081 and the one or more patient's helping hands on record until an ambulance from the nearby medical facility arrives or the emergency is over.

Figure 13:
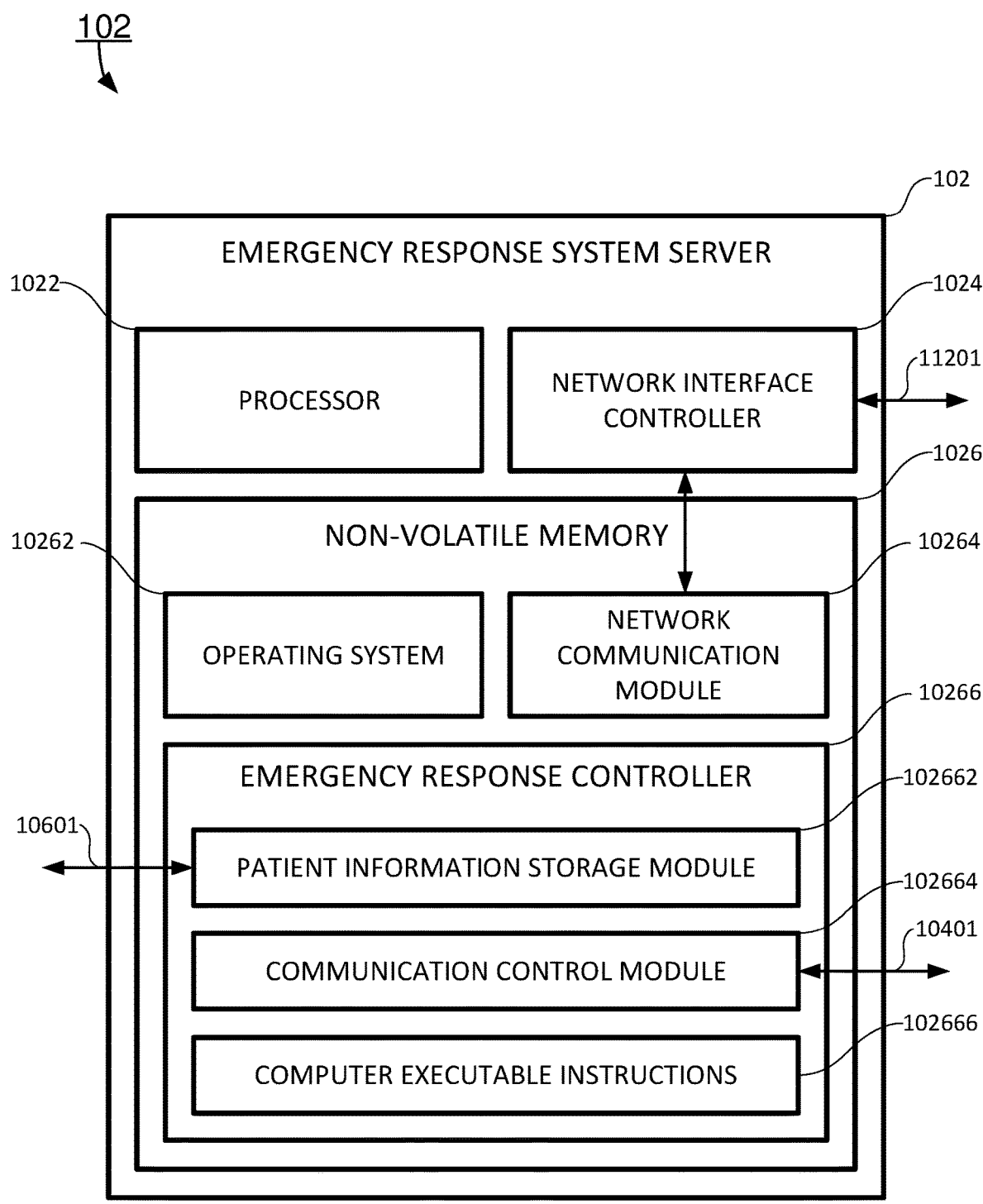
FIG. 13 illustrates a block diagram of an emergency response system server according to certain embodiments of the present disclosure.

In certain embodiments, as shown in FIG. 13, the emergency response system server 102 includes: a processor 1022 for controlling operations of the emergency response system 100, a network interface controller 1024 connected to the communication network 110 through a firewall connector 11201 over a firewall 112, and a non-volatile memory 1026 for storing an operating system 10262, a network communication module 10264, and an emergency response controller 10266. The emergency response controller 10266 includes a patient information storage module 102662 for accessing the patient database 106 through a database connector 10601, a communication control module 102664 for facilitating communication to the communication system 104 through a communication system connector 10401, and computer executable instructions 102666.

In certain embodiments, when executed by the processor 1022, the computer executable instructions 102666 performs one or more of following operations: receiving, from the patient response device 120, an emergency voice call through the communication system 104 when the patient response device 120 is activated by the patient 130 pressing the emergency button 1201 and the patient 130 speaking to the microphone 12091 with a predetermined distinctive phrase when an emergency occurs, notifying the live emergency responder 1081 of the nearby emergency dispatch center 108 of the emergency along with patient's GPS location information, and patient information including contact information of patient's helping hands on record, and connecting, via the patient response device 120 carried by the patient 130, to the patient's helping hands on record and the nearby medical facility through the communication control module 102664 to coordinate immediate medical assistance to the patient 130.

In certain embodiments, the computer executable instructions 102666 also performs one or more of following operations: retrieving, by the patient information storage module 102662, patient information from the patient database 106, transmitting, by the communication control module 102664, a set of patient specific medical assistance instructions through the communication system connector 10401 and the live emergency responder 1081 for the patient 130 to follow including instructing the patient to take one or more patient specific emergency medicines stored in the emergency medicine storage 1208 of the patient response device 120, and the patient 130 continues to communicate with the live emergency responder 1081 and the one or more patient's helping hands on record until an ambulance from the nearby medical facility arrives or the emergency is over.

Figure 14:
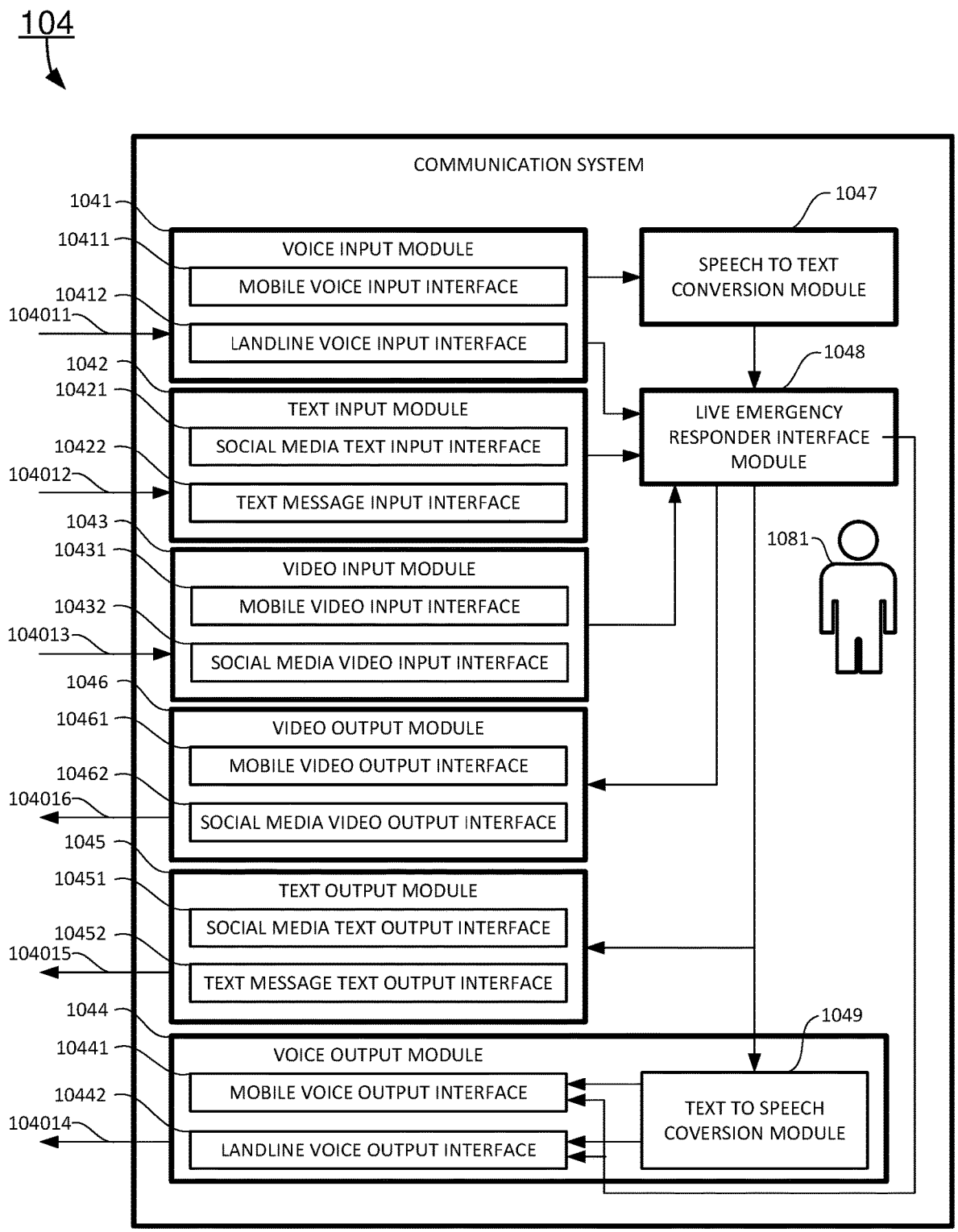
FIG. 14 illustrates a block diagram of a communication system according to certain embodiments of the present disclosure.

In certain embodiments, as shown in FIG. 14, the communication system 104 includes: a voice input module 1041 having a mobile voice input interface 10411 to receive mobile voice calls, and a landline voice input interface 10412 to receive landline voice calls, a text input module 1042 having a social media text input interface 10421 to receive text messages through a variety of social media platforms, and a text message input interface 10422 to receive text messages through mobile phones, a video input module 1043 having a mobile video input interface 10431 to receive videotelephony calls over the mobile phones, and a social media video input interface 10432 to receive videotelephony calls through the variety of social media platforms, a voice output module 1044 having a mobile voice output interface 10441 to make mobile voice calls, and a landline voice output interface 10442 to make landline voice calls, a text output module 1045 having a social media text output interface 10451 to transmit text messages through the variety of social media platforms, and a text message output interface 10452 to transmit text messages through the mobile phones, a video output module 1046 having a mobile video output interface 10461 to make videotelephony calls over the mobile phones, and a social media video output interface 10462 to make videotelephony calls through the variety of social media platforms, a speech to text conversion module 1047 for converting voice input to text input, a live emergency responder interface module 1048 for the live emergency responder 1081 to receive and make conference calls among the patient 130, the live emergency responder 1081, the patient's helping hands on record and the nearby medical facility through voice calls, text messages, and videotelephony calls, and a text to speech conversion module 1049 to make voice calls to the patient 130 through the patient response device 120.

In certain embodiments, the social media platforms include, but not limited to: Facebook, Youtube, WhatsApp, Messenger, WeChat, Instagram, QQ, Tumblr, Qzone, Tik Tok, Sina Weibo, Twitter, Reddit, Baidu Tieba, LinkedIn, Viber, Snappchat, and Pinterest and various combination of these social media platforms.

The communication system connector 10401 includes: a voice input terminal 104011 connected to the voice input module 1041, a text input terminal 104012 connected to the text input module 1042, a video input terminal 104013 connected to the video input module 1043, a voice output terminal 104014 connected to the voice output module 1044, a text output terminal 104015 connected to the text output module 1045, and a video output terminal 104016 connected to the video output module 1046.

Figure 15:
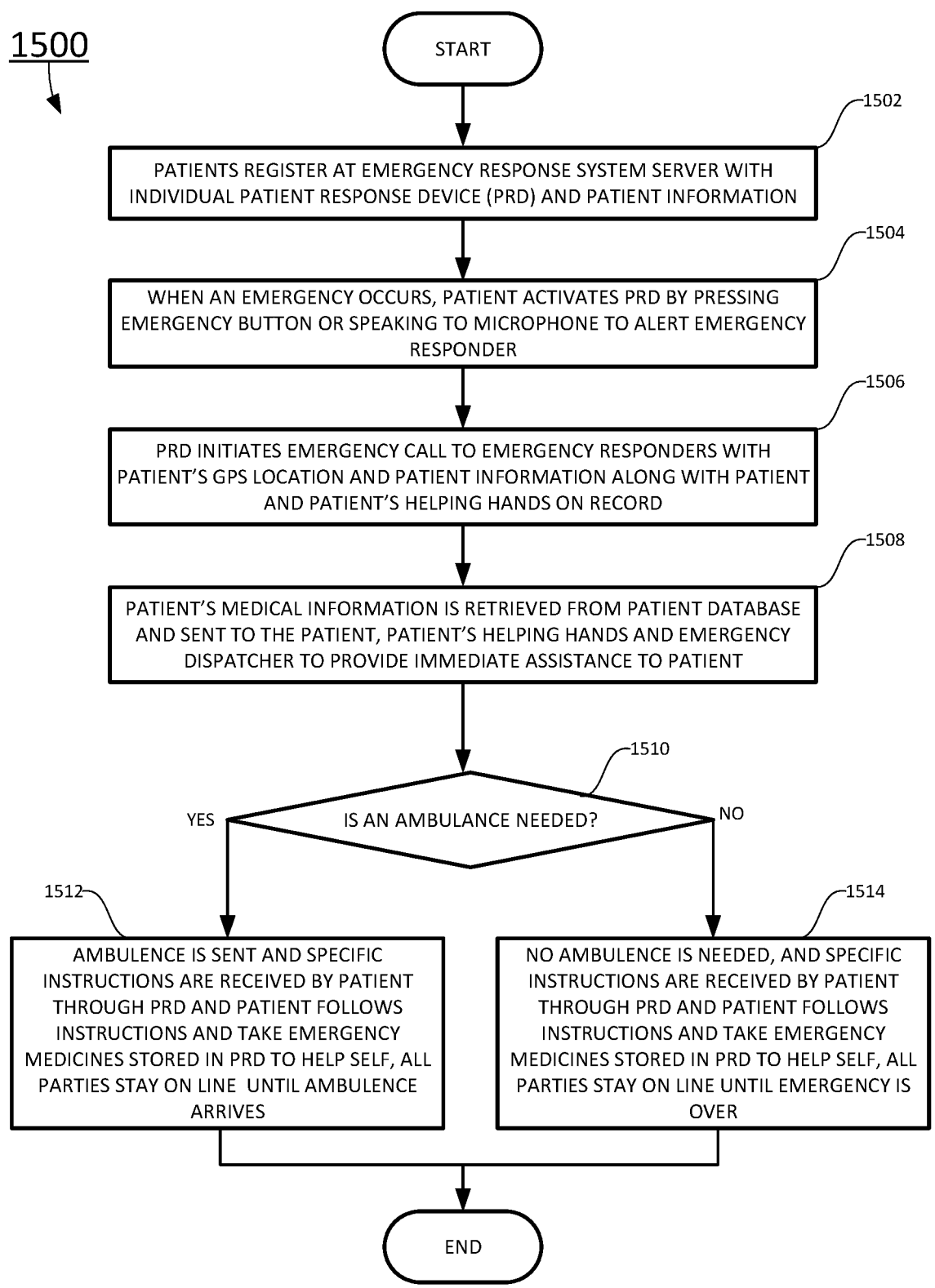
FIG. 15 shows a flow chart of a method of using a patient response device according to certain embodiments of the present disclosure.

In yet another aspect, the present disclosure relates to a method of using a patient response device 120. FIG. 15 shows a flow chart of the method 1500 of using the patient response device 120 according to certain embodiments of the present disclosure.

At block 1502, each of a group of patients 130 register the patient 130 with individual patient information, and a corresponding patient response device 120 at the emergency response system server 102 of the emergency response system 100, one patient response device 120 for each patient 130. The patient information of each of the patients 130 is stored in a patient database 106 of the emergency response system 100. The emergency response system 100 includes a network of emergency dispatch centers 108 to provide immediate emergency assistance to the patients 130 when emergencies occur to the registered patients 130.

At block 1504, an emergency response system indicator 1203 of the patient response device 120 is lit in green color indicating the patient 130 is in normal condition. When an emergency occurs to the patient 130, the patient 130 activates the patient response device 120. In one embodiment, the patient 130 activates the patient response device 120 by pressing the emergency button 1201 of the patient response device 120 carried by the patient 130 to alert one or more live emergency responders 1081. When the emergency button 1201 is pressed for a predetermined period of time by the patient 130, the patient response device 120 initiate at least voice communication with the emergency response system server 102 and the communication system 104 directly. In one embodiment, the predetermined period of time may be set as three seconds. When the patient 130 presses the emergency button 1201 for longer than three seconds, the patient response device 120 determines that the patient 130 does have an emergency. When the patient 130 presses the emergency button 1201 for less than three seconds, the patient response device 120 determines that the patient 130 does not have an emergency, and the emergency button 1201 was pressed by accident. This is designed to distinguish a real emergency and a false alarm.

In another embodiment, the patient 130 activates the patient response device 120 by speaking to the microphone 12091 of the patient response device 120 carried by the patient 130 with the predetermined distinctive phrase to alert one or more live emergency responders 1081. The emergency response system indicator 1203 of the patient response device 120 turns red indicating the patient 130 is in an emergency.

At block 1506, the patient response device 120 initiates an emergency call to a nearby emergency dispatch center 108 to notify the live emergency responder 1081 with the patient's GPS location information and patient information including contact information of one or more patient's helping hands on record. The patient response device 120 is connected with the live emergency responder 1081, one or more patient's helping hands on record, and a nearby medical facility through landline or wireless voice calls, wireless videotelephony calls, text messages, and information exchanges through various social media platforms.

At block 1508, the patient 130's medical information is received by the emergency response system server 102 from the patient response device 120 and retrieved from the patient database 106, and sent to the patient 130 to assist the patient 130, the patient's helping hands on record, and the live emergency responder 1081 to provide immediate assistance to the patient 130.

At query block 1510, the live emergency responder 1081 determines whether an ambulance is needed. If the ambulance is needed is needed, the method 600 proceeds to block 612. Otherwise, the method 600 proceeds to block 614.

At block 1512, when the ambulance is needed, the live emergency responder 1081 notifies the nearby emergency medical facility to send the ambulance and patient specific professional staffs to assist the patient 130. In the meantime, patient specific medical assistance instructions for the patient 130 to follow are sent to the patient 130. These patient specific medical assistance instructions include necessary steps the patient 130 can perform and instructions to take one or more patient specific emergency medicines stored in the emergency medicine storage 1208 of the patient response device 120, until the ambulance and the patient specific professional staffs arrive.

At block 1514, when the ambulance is not needed, patient specific medical assistance instructions for the patient 130 to follow are sent to the patient 130. These patient specific medical assistance instructions include necessary steps the patient 130 can perform and instructions to take one or more patient specific emergency medicines stored in the emergency medicine storage 1208 of the patient response device 120. The patient 130 stays online with the live emergency responder 1081, the patient's helping hands on record, and emergency medical staff until the emergency is over.

The foregoing description of the exemplary embodiments of the disclosure has been presented only for the purposes of illustration and description and is not intended to be exhaustive or to limit the disclosure to the precise forms disclosed. Many modifications and variations are possible considering the above teaching.

The embodiments were chosen and described in order to explain the principles of the disclosure and their practical application to enable others skilled in the art to utilize the disclosure and various embodiments and with various modifications as are suited to the particular use contemplated. Alternative embodiments will become apparent to those skilled in the art to which the present disclosure pertains without departing from its spirit and scope. Accordingly, the scope of the present disclosure is defined by the appended claims rather than the foregoing description and the exemplary embodiments described therein.

What is claimed is:

1. A patient response device, comprises:
   a processor, wherein the processor controls operations of the patient response device;
   a network interface controller, wherein the network interface controller facilitates the communication among the patient response device, an emergency response system server and a communication system of an emergency response system;
   an emergency medicine storage, wherein the emergency medicine storage comprises one or more emergency medicine compartments, where one or more patient specific emergency medicines for a patient are stored; and
   a non-volatile memory, wherein the non-volatile memory stores an operating system, a GPS module, and a patient response device controller having a patient information storage module, a patient communication control module, and computer executable instructions, wherein the GPS module detects the GPS location of the patient carrying the patient response device, the patient information storage module stores patient's information, and the patient communication control module facilitates communication through the network interface controller to the emergency response system server and the communication system over a communication network, when executed by the processor, the computer executable instructions performs one or more of following operations:
   receiving an emergency signal from an activated patient response device when an emergency occurs to the patient, wherein the patient response device is activated by the patient by pressing an emergency button of the patient response device, and by speaking to a microphone of the patient response device with a predetermined distinctive phrase;
   initiating, by the patient response device, an emergency call to a nearby emergency dispatch center to notify a live emergency responder with the patient's GPS location information and patient information including contact information of patient's helping hands on record;
   connecting, by the patient response device, the patient's helping hands on record and a nearby medical facility through the patient communication control module to coordinate immediate medical assistance to the patient based on the patient information retrieved from a patient database of the emergency response system and from the patient information storage module;
   receiving, by the patient through the patient response device, a set of patient specific medical assistance instructions from the live emergency responder for the patient to follow including instructing the patient to take one or more patient specific emergency medicines stored in the emergency medicine storage of the patient response device; and
   continuing, by the patient through the patient response device, communicating with the live emergency responder and the one or more patient's helping hands on record until an ambulance from the nearby medical facility arrives or the emergency is over.

2. The patient response device according to claim 1, wherein the patient response device comprises:

at least the microphone and a speaker for the patient to make and receive voice calls, and to activate the patient response device by speaking to the microphone with the predetermined distinctive phrase; and a patient response device indicator, wherein the patient response device indicator is in green color when the patient is in normal condition, and patient response device indicator is in red color when the patient is in an emergency condition and the patient has activated the patient response device.

3. The patient response device according to claim 1, wherein the patient response device further comprises a display screen to receive and display text messages and a camera to carry out videotelephony calls.

4. The patient response device according to claim 1, wherein the communication among the patient, the live emergency responder, the patient's helping hands on record and the nearby medical facility comprises:
   mobile voice calls;
   mobile videotelephony calls;
   landline voice calls;
   videotelephony calls over the Internet;
   text messages over a mobile phone;
   text messages over a plurality of social media platforms; and
   videotelephony calls over the plurality of social media platforms.

5. The patient response device according to claim 1, wherein the communication network comprises a wireless personal area network (WPAN) having a Wi-Fi network, a Bluetooth network, an infrared network, and a Zigbee network, a wireless local area network (WLAN), a wireless metropolitan area network (WMAN), a wireless wide area network (WWAN), a cellular network, and a mobile communication network.

6. The patient response device according to claim 1, wherein the patient response device comprises:
   a portable patient response device to be carried with the patient wherein the portable patient response device stores one or more patient specific emergency medicines;
   a stationary patient response device to be placed at home or work place of the patient wherein the stationary patient response device stores one or more patient specific emergency medicines; and
   a plurality of public stationary patient response devices to be placed in public places wherein each of the plurality of public stationary patient response devices stores at least one of a plurality of common emergency medicines.

7. The patient response device according to claim 6, wherein the portable patient response device comprises:
   a lanyard holder to attach the patient response device to the patient through a lanyard;
   a battery charger;
   a SIM card slot, wherein a wireless communication SIM card is placed in the SIM card slot to support wireless communication; and
   an emergency flash light.

8. The patient response device according to claim 6, wherein the portable patient response device comprises: one or more speed dial keys to be programed for the patient to contact one or more frequent callers.

9. An emergency response system, comprising:
   an emergency response system server, wherein each of a plurality of patients and a corresponding patient response device each patient carries are registered at the emergency response system server, and the emergency response system server provides immediate emergency assistance to each of the plurality of patients when emergencies occur;
   a patient database connected to and accessible by the emergency response system server, wherein the patient database stores patient information of the plurality of patients, wherein the patient information comprises personal information, medical history, patient contact information, and contact information of patient's helping hands and local medical facilities to be notified of each patient;
   a communication system connected to the emergency response system server, wherein the communication system provides voice, text, and video communication over a communication network among the patient, one or more live emergency responders from a nearby emergency dispatch center, one or more patient's helping hands on record, and one or more nearby medical facilities to provide immediate emergency assistance to the patient when emergency occurs; wherein the patient's helping hands include all family members, relatives, friends, neighbors, guardians, bystanders, local emergency or non-emergency medical facilities, community rescue members and trained CPR volunteers, and anyone who is nearby and is able to offer assistance, and
   a plurality of patient response devices, wherein each patient carries a corresponding patient response device, and each patient response device comprises an emergency button and a microphone for the patient to activate the patient response device and initiate at least voice communication with the emergency response system server and the communication system directly, and an emergency medicine storage for storing one or more patient specific emergency medicines to be used when emergency occurs;
   wherein a patient response device indicator of the patient response device is lit in green light indicating the patient is in normal condition, when an emergency occurs to a patient, the patient activates the patient response device, the patient response device indicator turns red indicating the patient is in an emergency, the patient response device initiates an emergency call to the nearby emergency dispatch center to notify a live emergency responder with the patient's GPS location information and patient information including contact information of patient's helping hands on record, the live emergency responder connects to one or more patient's helping hands on record and a nearby medical facility to coordinate immediate medical assistance to the patient based on the patient information received and retrieved from the patient database, and the live emergency responder and the emergency response system server provide patient specific medical assistance instructions for the patient to follow including instructing the patient to take one or more patient specific emergency medicines stored in the emergency medicine storage of the patient response device, and the patient continues to communicate with the live emergency responder and the one or more patient's helping hands on record until an ambulance from the nearby medical facility arrives or the emergency is over.

10. The emergency response system according to claim 9, wherein the emergency response system server comprises:
    a processor for controlling operations of the emergency response system;

a network interface controller connected to the communication network through a firewall connector over a firewall; and a non-volatile memory, wherein the non-volatile memory stores an operating system, a network communication module, and an emergency response controller having a patient information storage module, a communication control module, and computer executable instructions, wherein the patient information storage module accesses the patient database through a database connector, and the communication control module facilitates communication to the communication system through a communication system connector, when executed by the processor, the computer executable instructions performs one or more of following operations:

receiving, from the patient response device, an emergency voice call through the communication system when the patient response device is activated by the patient pressing the emergency button and the patient speaking to the microphone with a predetermined distinctive phrase when an emergency occurs;

notifying the live emergency responder of the nearby emergency dispatch center of the emergency along with patient's GPS location information, and patient information including contact information of patient's helping hands on record;

connecting, via the patient response device carried by the patient, to the patient's helping hands on record and the nearby medical facility through the communication control module to coordinate immediate medical assistance to the patient;

retrieving, by the patient information storage module, patient information from the patient database;

transmitting, by the communication control module, a set of patient specific medical assistance instructions through the communication system connector and the live emergency responder for the patient to follow including instructing the patient to take one or more patient specific emergency medicines stored in the emergency medicine storage of the patient response device, and the patient continuing to communicate with the live emergency responder and the one or more patient's helping hands on record until an ambulance from the nearby medical facility arrives or the emergency is over.

11. The emergency response system according to claim 10, wherein the communication system comprises:

a voice input module having a mobile voice input interface to receive mobile voice calls, and a landline voice input interface to receive landline voice calls;

a text input module having a social media text input interface to receive text messages through the plurality of social media platforms, and a text message input interface to receive text messages through mobile phones;

a video input module having a mobile video input interface to receive videotelephony calls over the mobile phones, and a social media video input interface to receive videotelephony calls through the plurality of social media platforms;

a voice output module having a mobile voice output interface to make mobile voice calls, and a landline voice output interface to make landline voice calls;

a text output module having a social media text output interface to transmit text messages through the plurality of social media platforms, and a text message output interface to transmit text messages through the mobile phones;

a video output module having a mobile video output interface to make videotelephony calls over the mobile phones, and a social media video output interface to make videotelephony calls through the plurality of social media platforms;

a speech to text conversion module, wherein the speech to text conversion module converts voice input to text input;

a live emergency responder interface module, wherein the live emergency responder interface module is used by the live emergency responder to receive and make conference calls among the patient, the live emergency responder, the patient's helping hands on record and the nearby medical facility through voice calls, text messages, and videotelephony calls; and a text to speech conversion module, wherein the text to speech conversion module makes voice calls to the patient through the patient response device.

12. The emergency response system according to claim 11, wherein the communication system connector comprises:

a voice input terminal connected to the voice input module;

a text input terminal connected to the text input module;

a video input terminal connected to the video input module;

a voice output terminal connected to the voice output module;

a text output terminal connected to the text output module; and a video output terminal connected to the video output module.

13. A method of using a patient response device, comprising:

registering, by a plurality of patients, each of the plurality of patients, and a plurality of patient response devices, one corresponding patient response device for each patient, at an emergency response system server of an emergency response system, wherein patient information of each of the plurality of patients is stored in a patient database of the emergency response system, and the emergency response system comprises a network of emergency dispatch centers 108 to provide immediate emergency assistance to the plurality of patients when emergencies occur to them;

activating, by a patient, the patient response device carried by the patient when an emergency occurs to the patient, and a patient response device indicator of the patient response device turns red indicating the patient is in an emergency condition, wherein the patient response device is activated by the patient pressing an emergency button of the patient response device and speaking to a microphone of the patient response device with a predetermined distinctive phrase;

initiating, by the patient response device, an emergency call to a nearby emergency dispatch center to notify a live emergency responder with the patient's GPS location information and patient information including contact information of patient's helping hands on record;

connecting, by the live emergency responder, to one or more patient's helping hands on record and a nearby medical facility to coordinate immediate medical assistance to the patient based on the patient information received and retrieved from the patient database;

providing, by the live emergency responder and the emergency response system server, patient specific medical assistance instructions for the patient to follow including instructing the patient to take one or more patient specific emergency medicines stored in an emergency medicine storage of the patient response device; and communicating, by the patient through a communication system of the emergency response system, with the live emergency responder and the one or more patient's helping hands on record until an ambulance from the nearby medical facility arrives.

14. The method of claim 13, wherein the emergency response system comprises:

the emergency response system server, wherein each of the plurality of patients and a corresponding patient response device each patient carries are registered at the emergency response system server, and the emergency response system server provides immediate emergency assistance to each of the plurality of patients when emergencies occur;

the patient database connected to and accessible by the emergency response system server, wherein the patient database stores patient information of the plurality of patients, wherein the patient information comprises personal information, medical history, patient contact information, and contact information of patient's helping hands on record and local medical facilities to be notified of each of the plurality of the patients;

the communication system connected to the emergency response system server, wherein the communication system provides voice, text, and video communication over a communication network among the patient, one or more live emergency responders from the nearby emergency dispatch center, one or more patient's helping hands on record, and one or more nearby medical facilities to provide immediate emergency assistance to the patient when emergency occurs; and the plurality of patient response devices, wherein each of the plurality of patients carries one corresponding patient response device, and each of the plurality of patient response devices comprises the emergency button for the patient to press and the microphone for the patient to speak to for activating the patient response device and initiating at least voice communication with the emergency response system server and the communication system directly, and the emergency medicine storage for storing one or more patient specific emergency medicines to be used when emergency occurs.

15. The method of claim 14, wherein the communication network comprises a wireless personal area network (WPAN) having a Wi-Fi network, a Bluetooth network, an infrared network, and a Zigbee network, a wireless local area network (WLAN), a wireless metropolitan area network (WMAN), a wireless wide area network (WWAN), a cellular network, and a mobile communication network.

16. The method of claim 15, the emergency response system server comprises:

a processor for controlling operations of the emergency response system;

a network interface controller connected to the communication network through a firewall connector over a firewall; and a non-volatile memory, wherein the non-volatile memory stores an operating system, a network communication module, and an emergency response controller having a patient information storage module, a communication control module, and computer executable instructions, wherein the patient information storage module accesses the patient database through a database connector, and the communication control module facilitates communication to the communication system through a communication system connector, when executed by the processor, the computer executable instructions performs one or more of following operations:

receiving, from a patient response device, an emergency voice call through the communication system when the patient response device is activated by the patient when an emergency occurs, wherein the patient response device is activated by the patient by pressing the emergency button of the patient response device, and by speaking to the microphone of the patient response device with a predetermined distinctive phrase;

notifying, the live emergency responder of the nearby emergency dispatch center of the emergency along with patient's GPS location information and patient information including contact information of patient's helping hands on record;

connecting, the patient response device carried by the patient to the patient's helping hands on record and a nearby medical facility through the communication control module to coordinate immediate medical assistance to the patient;

retrieving, by the patient information storage module, patient information from the patient database;

receiving, via the communication control module, a set of patient specific medical assistance instructions through the communication system connector and the live emergency responder for the patient to follow, while the patient takes the patient specific emergency medicines stored in the emergency medicine storage of the patient response device; and communicating, by the patient, the live emergency responder and one or more patient's helping hands on record until an ambulance from the nearby medical facility arrives or the emergency is over.

17. The method of claim 16, wherein the patient response device comprises at least the microphone and a speaker for the patient to make and receive voice calls, and to activate the patient response device by speaking to the microphone with the predetermined distinctive phrase.

18. The method of claim 17, wherein the patient response device further comprises a display screen to receive and display text messages and a camera to carry out videotelephony calls.

19. The method of claim 18, wherein the communication among the patient, the live emergency responder, the patient's helping hands on record and the nearby medical facility comprises:

a mobile voice call;
a mobile videotelephony call;
a landline voice call;
a videotelephony call over the Internet;
a text message over a mobile phone;
a text message over a plurality of social media platforms; and
a videotelephony call over the plurality of social media platforms; and wherein the communication system connector comprises:
a voice input terminal connected to a voice input module;
a text input terminal connected to a text input module;
a video input terminal connected to a video input module;

a voice output terminal connected to a voice output module;

a text output terminal connected to a text output module; and a video output terminal connected to a video output module.

20. The method of claim 13, wherein the patient response device comprises:

a portable patient response device to be carried with the patient wherein the portable patient response device stores one or more patient specific emergency medicines;

a stationary patient response device to be placed at home or work place of the patient wherein the stationary patient response device stores one or more patient specific emergency medicines; and a plurality of public stationary patient response devices to be placed in public places wherein each of the plurality of public stationary patient response devices stores at least one of a plurality of common emergency medicines.

\* \* \* \* \*